US012806169B2

(12) United States Patent
Vivier

(10) Patent No.: US 12,806,169 B2
(45) Date of Patent: Nov. 24, 2026

(54) PUTRESCINE TOPICAL FORMULATIONS

(71) Applicant: VIVIER CANADA INC., Vaudreuil-Dorion (CA)

(72) Inventor: Ghislain Vivier, Saint-Lazare (CA)

(73) Assignee: VIVIER CANADA INC., Vaudreuil-Dorion (CA)

( * ) Notice: Subject to any disclaimer, the term of this patent is extended or adjusted under 35 U.S.C. 154(b) by 0 days.

(21) Appl. No.: 18/423,569

(22) Filed: Jan. 26, 2024

(65) Prior Publication Data

US 2024/0216329 A1 Jul. 4, 2024

Related U.S. Application Data

(63) Continuation of application No. 18/046,221, filed on Oct. 13, 2022, now abandoned, which is a continuation of application No. 16/613,719, filed as application No. PCT/CA2018/050771 on Jun. 22, 2018, now abandoned.

(60) Provisional application No. 62/524,075, filed on Jun. 23, 2017.

(51) Int. Cl.

| | |
|---|---|
| ***A61K 31/375*** | (2006.01) |
| ***A61K 8/04*** | (2006.01) |
| ***A61K 8/41*** | (2006.01) |
| ***A61K 8/67*** | (2006.01) |
| ***A61K 9/00*** | (2006.01) |
| ***A61K 9/06*** | (2006.01) |
| ***A61K 47/14*** | (2017.01) |
| ***A61K 47/18*** | (2017.01) |
| ***A61K 47/22*** | (2006.01) |
| ***A61K 47/26*** | (2006.01) |
| ***A61K 47/32*** | (2006.01) |
| ***A61K 47/34*** | (2017.01) |
| ***A61K 47/36*** | (2006.01) |
| ***A61K 47/42*** | (2017.01) |
| ***A61Q 19/08*** | (2006.01) |

(52) U.S. Cl.

CPC .............. *A61K 31/375* (2013.01); *A61K 8/04* (2013.01); *A61K 8/41* (2013.01); *A61K 8/676* (2013.01); *A61K 9/0014* (2013.01); *A61K 9/06* (2013.01); *A61K 47/14* (2013.01); *A61K 47/18* (2013.01); *A61K 47/22* (2013.01); *A61K 47/26* (2013.01); *A61K 47/32* (2013.01); *A61K 47/34* (2013.01); *A61K 47/36* (2013.01); *A61K 47/42* (2013.01); *A61Q 19/08* (2013.01); *A61K 2800/522* (2013.01); *A61K 2800/805* (2013.01)

(58) Field of Classification Search

None

See application file for complete search history.

(56) References Cited

U.S. PATENT DOCUMENTS

| | | | | |
|---|---|---|---|---|
| 5,977,039 A * | 11/1999 | Gordon | A47K 7/02 | 510/159 |
| 7,404,967 B2 * | 7/2008 | Hahn | A61K 33/24 | 514/846 |
| 8,409,154 B2 * | 4/2013 | Mitra | A61P 17/00 | 4/537 |
| 2005/0209131 A1 * | 9/2005 | Singleton | A61K 8/64 | 424/70.14 |
| 2008/0124312 A1 * | 5/2008 | Lovaas | A61Q 19/08 | 424/94.1 |
| 2008/0125482 A1 | 5/2008 | Vivier et al. | | |

FOREIGN PATENT DOCUMENTS

| | | | | |
|---|---|---|---|---|
| CA | 2508095 A1 * | 11/2006 | A61K 8/44 |
| WO | 9804245 A1 | 2/1998 | |
| WO | 2006048671 A1 | 5/2006 | |
| WO | 2009067799 A1 | 6/2009 | |
| WO | WO-2012013418 A2 * | 2/2012 | A61K 45/06 |
| WO | 201890149 A1 | 5/2018 | |

OTHER PUBLICATIONS

GrenzCine Eye (Vivier Product Information, available online Feb. 4, 2017) (Year: 2017).*

Dolynchuk KN et al., Effect of Putrescine on tissue transglutaminase activity in wounds: Decreased breaking strength and increased matrix Fucoprotein solubility, Plast Reconstr. Surg. 1994; 93: p. 567-573—Abstract.

Lynde. C.W. Moisturizers: What they are and how they work. Skin Therapy Letter, 2001.

Sheokand, Sunita, Anita Kumari, and Veena Sawhney. "Effect of Nitric Oxide and Putrescine on Antioxidative Responses under NaCl Stress in Chickpea Plants." Physiology and molecular biology of plants: an international journal of functional plant biology 14.4 (2008): 355-362. PMC. Web. Jun. 14, 2017.

Soda K. et al., Spermine, a natural polyamine, suppresses LFA-1 expression on human lymphocyte. J. Immunol. 175, 237-45 (2005)—Abstract.

Tajima S, Pinnell SR, Ascorbic acid preferentially enhances type I and III collagen transcription in human skin fibroblasts. J.Derm Science. 11:250-53, 1996. 2Traikovich SS.

Traikovich S.S., Use of topical ascorbic acid and its effects on photo damaged skin topography. Arch Otolaryngol Head Neck Surg 125:1091-98, 1999.

Vivier™ Pharma, "GrenzCine™ Eye 11-120-ZZ-80074-R", published online on Feb. 4, 2017. SuperiorSkin, "GrenzCine™ Serum", published online on Feb. 11, 2017.

Vivier™ Pharma, "Introducing a skin care revolution: GrenzCinerm Serum** Slow-Release", published online on Feb. 4, 2017.

(Continued)

*Primary Examiner* — Melissa S Mercier

(74) *Attorney, Agent, or Firm* — Julie Gauvreau; Lavery, de Billy, L.L.P.

(57) ABSTRACT

The present invention describes complex topical aqueous compositions for the effective delivery of active ingredients such as putrescine and Vitamin C into the skin. These compositions may be used in a variety of cosmetic and therapeutic applications including for reducing or preventing skin's signs of aging, for promoting wound healing, for reducing or preventing the formation of hypertrophic scar tissue, for reducing or preventing skin irritation and/or inflammation.

6 Claims, No Drawings

(56) References Cited

OTHER PUBLICATIONS

Vivier™ Pharma, "Vivier™ Pharma Launches GrenzCine™ Serum** ", published online on May 5, 2017.
Zhang M. et al., Spermine inhibits proinflammatory cytokine synthesis in human mononuclear cells: a counterregulatory mechanism that restrains the immune response. J. Exp. Med. 185, 1759-68 (1997).
Office Action dated Aug. 21, 2024 issued by the Canadian Intellectual Property Office in CA3,067,905.
International Search Report dated Aug. 15, 2018 issued by the Canadian Intellectual Property Office in PCT/CA2018/050771.

* cited by examiner

PUTRESCINE TOPICAL FORMULATIONS

CROSS REFERENCE TO RELATED APPLICATIONS

This application is a continuation application of U.S. patent application Ser. No. 18/046,221, now abandoned which is a continuation application of U.S. patent application Ser. No. 16/613,719, now abandoned, which is a National Entry Application of PCT application Serial No CA2018/050771 filed on Jun. 22, 2018 and published in English under PCT Article 21(2), which itself claims benefit of U.S. provisional application Ser. No. 62/524,075, filed on Jun. 23, 2017. All documents above are incorporated herein in their entirety by reference.

FIELD OF THE INVENTION

The present invention relates to complex, stable formulations comprising multiple active ingredients including primary polyamines and/or Vitamin C and uses thereof for stimulating wound healing and reducing signs of aging including skin thickening and hyperpigmentation. The present invention also relates to a process for obtaining such formulations.

BACKGROUND OF THE INVENTION

Skin is a physical barrier to the environment. In mammals, it is composed of multiple layers of ectodermal tissue, and guards the underlying muscles, bones, ligaments and internal organs. It is the alteration of the barrier properties and actual damage to this barrier that causes numerous skin conditions.

The epidermis and the dermis, separated by the basal membrane (EDJ (epidermal—dermal junction) or Grenz Zone) constitute the cutaneous covering on the hypoderm. The epidermis is the most superficial layer of the skin and provides its resistance and impermeability. Alteration of this layer will negatively affect perceived quality of the skin and will eventually lead to cutaneous aging. The dermis, the internal layer of the skin, is a conjunctive tissue composed of cells (essentially fibroblasts) dispersed in a complex medium called the extracellular matrix (ECM). This matrix consists of collagen and elastin fibers, glycoproteins (fibronectin and laminin) and proteoglycans. The extracellular matrix serves as a structure for the cells, allowing tissues and organs to cohere in pluricellular organisms. The EDJ, which attaches the epidermis and the dermis of the skin is vitally important due to the roles it plays in cellular communication, nutrient exchange and absorption, and other skin functions. The layers of the epidermis are continually moving upward, throwing their "contents" overboard, flattening, building up at the surface and then eventually sloughing off to make room for the cells right behind them. This natural movement or "keratinization" of the skin is an integral part of skin renewal and healing. It would not be possible without the epidermal-dermal Junction (EDJ) maintaining the relationship between the two main layers of skin, allowing for healthy communication from the top, all the way to the bottom.

The EDJ is also responsible for the exchange of nutrients back and forth from the epidermis to the dermis. These nutrients are carried in the blood from the food we eat and absorbed through the pores from topical application. Vitamins, antioxidants, acids and other nutrients are needed for DNA repair, new cell production, protection from outside elements and oxidative stress and more. In youth, this junction is a healthy, wavy terrain. The finger-like waves in the junction, called rete ridges, form the interlocking connection between the dermis and epidermis. They increase the surface area of the epidermis that is exposed to these blood vessels and the needed nutrients. Without this nutrient exchange, skin would suffer from premature aging and damage.

As we age or stress our skin, it tends to flatten out. If the junction completely flat lines, no pun intended, the communication and nutrient exchange comes to a halt. So, in order to maintain skin healthy—and youth—you want to keep the communication open and the EDJ's rete waves as wavy as possible. Maintaining EDJ functioning can be helped by proper diet and topical skin supplementation as well as limiting over exfoliation, over exposure to harsh elements and any other form of stress or trauma.

Dry skin is one of the most common skin problems. It can be treated by applying moisturizers. Moisturizers are oily substances which are used to replace natural skin oils, to cover tiny fissures and to provide a protective film. Four types of moisturizers have been described according to their mechanism of action: Occlusive, Humectants, Emollients, and Protein Rejuvenators. Occlusive moisturizers (e.g., petroleum in a minimum concentration of 5%, lanolin, mineral oil, silicones (such as dimethicone)) are substances which physically block trans-epidermal water loss (TEWL) in the stratum corneum. Humectants (e.g., glycerin, sorbitol, urea, alpha-hydroxy acids, and other sugars) work by attracting trans-epidermal water to the skin to improve hydration of the stratum corneum. However, their chronic use may contribute to continuous evaporation from the skin and may under certain conditions, exacerbate dryness. Emollients (e.g., Vitamin E, fatty acids, cholesterol, squalene/squalane, structural lipids (e.g., ceramide), stearic, linoleic, linolenic and lauric acids (found in palm oil and coconut oil) smooth skin by filling spaces between skin flakes and droplets of oil. Some emollients (long chain fatty acids) act by influencing skin's physiology and pathology through their action on skin barrier function, eicosanoid production, cell signaling and membrane fluidity. Moisturizers containing collagen and other large proteins (e.g., elastin and keratin) are said to rejuvenate the skin by providing essential proteins (however, efficient dermal delivery of such proteins often remains a challenge due to their large size). Moisturizers and their effects are reviewed in C. W. Lynde. Moisturizers: What they are and how they work. Skin Therapy Letter, 2001; http://www.skintherapyletter.com/2001/6.13/2.html.

Cutaneous aging is a complex phenomenon responsible for progressive changes of the skin. Aging of the skin results from two processes: (1) an intrinsic process, corresponding to chronological aging, and (2) an extrinsic process resulting mainly from the deleterious effect of exposure environmental stresses. Genetic, UV exposure, climatic factors (harshness/wind/cold/warm), pollution (chemical, free radicals, contaminant, nitrogen oxide, metals), alcohol consumption and smoking are factors involved in cutaneous aging.

Scar tissue is formed during healing of wounds following for example traumatic injury, burn and surgery (including cosmetic surgery). Often unpredictably, hypertrophy of the scar tissue occurs. Hypertrophic scar formation is characterized by the accumulation of collagen type III out of proportion to collagen type I. During skin wound healing it appears that type III procollagen amino peptide (PIIP) is cross-linked to other components of the wound matrix, such as fibrin and fibronectin, by tissue transglutaminase. Such cross-linking is thought to contribute to tissue hypertrophy and disproportionate scarring. Common treatment of hypertrophic scar tissue includes the use of drugs with potentially serious side effects (e.g., corticosteroid injection) and invasive procedures including surgical excision or cryotherapy.

Human growth factors (HGFs) have been attributed to many rejuvenating properties and are used as anti-aging agents and alternative wound healers. Many growth factors such as EGF and TGF-B are large proteins, which do not penetrate the skin well. They are also very unstable and often lose their activity within days in water or even as solids at normal temperatures. Furthermore, there are more and more concerns that at certain concentrations and over certain durations of application they can cause cells to over-proliferate and increase the risk of developing cancer and other health problems.

Primary polyamines (polyazaalkanes) have long been known as antioxidants. (see for example, Zhang M. et al., Spermine inhibits proinflammatory cytokine synthesis in human mononuclear cells: a counterregulatory mechanism that restrains the immune response. J. Exp. Med. 185, 1759-68 (1997); Soda K. et al., Spermine, a natural polyamine, suppresses LFA-1 expression on human lymphocyte. J. Immunol. 175, 237-45 (2005); and Soda K. et al., Polyamines' anti-aging effects. Food style 21, 10(10), 43-54 (2006); Sheokand et al., Sheokand S, Kumari A, Sawhney V. Effect of nitric oxide and putrescine on antioxidative responses under NaCl stress in chickpea plants. Physiology and molecular biology of plants: an international journal of functional plant biology. 2008; 14(4): 355-362). Recently, these compounds are attracting more and more interests as they have been shown to reduce skin inflammation and irritation and to be highly effective wound healing agents. Their effect on wound healing and hypertrophic scarring is thought to be due, at least partly, to their transglutaminase inhibiting activity which reduces type III pro-collagen cross-linking to components of the wound extracellular matrix. In addition to their effects on skin irritation, inflammation and on wound healing, primary polyamines have also been identified as useful agents for increasing skin thickness/preventing thin skin and also to prevent and/or reduce various other skin's signs of ageing (see for example U.S. Pat. No. 5,885,982, CA 2,706,630 and WO 2009/067799; and Dolynchuk K N et al., Effect of Putrescine on tissue transglutaminase activity in wounds: Decreased breaking strength and increased matrix Fucoprotein solubility, Plast Reconstr. Surg. 1994; 93: page 567-573.

Examples of primary polyamines include aminoacetonitrile, dansylcadaverine (1,5 diaminopentane), spermidine, and putrescine (1,4 diaminobutane). Putrescine is a natural compound that is related to cadaverine; both are produced by the breakdown of amino acids in living and dead organisms. The two compounds are largely responsible for the foul odor of putrefying flesh but are also found in other conditions (e.g., bad breadth). They are also found in semen and some microalgae, together with related molecules like spermine and spermidine. Putrescine is synthesized in small quantities by healthy living cells by the action of ornithine decarboxylase.

U.S. Pat. No. 5,885,982 (Dolynchuk) describes a method of preventing hypertrophic scar in human dermal wounds by applying a topical inhibitor of fibroblast tissue transglutaminase. Putrescine was shown to reduce collagen cross-linking in vitro and in vivo resulting in a softer and a more rapidly mature-looking scar as compared to controls. The negative side effects, typical of steroid injection, were not seen. Studies done on human harvested scars revealed an increase in apoptosis of scar fibroblasts which lead to a less active scar than seen with other methods of treatment.

Canadian patent application CA 2,706,630 (Dolynchuk, K.) further shows that putrescine provides beneficial effects on the epidermis of eroded skin increasing its barrier function as well as the thickness of the stratum lucidum in animals and the inner strata of human epidermis. The presence of topical polyamines such as putrescine enhances the cellular regenerative mechanisms and creates a robust grenz layer. These are typically reduced by inflammation, steroids and ageing effects, the recovery of which, results in a more youthful looking and functionally stable skin.

Vitamin C (also known as ascorbic acid and derivatives (e.g., ascorbyl palmitate, 3-O-ethyl ascorbic acid) is another well-known powerful antiaging and wound healing agent. Vitamin C deficiency causes spontaneous breakdown of wounds in the absence of infection in many surgery patients. Furthermore, evidence from the scientific literature shows that Vitamin C can increase collagen production in skin fibroblasts (1), counter skin damage associated with photo aging (2) and reduce the inflammation and erythema of sunburn (3). Ultimately Vitamin C helps reduce the expression of skin aging, translated into the appearance of fine lines or wrinkles in the skin.

In mammals, Vitamin C is involved in all phases of wound healing. It is necessary for a normal response to physiological stressors, with this need increasing during times of injury. Events that cause wounding, including trauma or surgery are physiological stressors that have been associated with a decrease in blood plasma Vitamin C levels. In the inflammatory phase it is required for neutrophil apoptosis and clearance. During the proliferative phase, Vitamin C has been shown to regulate synthesis, maturation, secretion and degradation of collagen. Also, evidence suggests that Vitamin C may improve wound healing by stimulating quiescent fibroblasts to divide and by promoting their migration into the wounded area. Furthermore, studies have shown that Vitamin C protects the skin by increasing the capacity of fibroblasts to repair potentially mutagenic DNA lesions and acts as a powerful antioxidant and immune system modulator.

The numerous beneficial effects attributed to Vitamin C makes it a particularly remarkable active agent in cosmetic and wound healing applications. Humans lack the ability to store Vitamin C, so it is important to continually replenish this vitamin through dietary means and/or other means such as topical supplementation (MacKay, Douglas, N D, and Miller, Alan L., ND, 2003).

Although a variety of chemical forms of Vitamin C are available commercially, not all forms are equally absorbed or active. As an antioxidant, Vitamin C needs to remain in its unoxidized form in order to be effective. However, it is particularly subject to oxidative degradation. Vitamin C is a moderately strong reducing agent, which makes it unstable in aqueous solutions, especially at high pHs. Paradoxically, water is one of the best solvents to dissolve many active ingredients including Vitamin C. Vitamin C is much less soluble in glycols such as propylene glycol (50 mg/ml) and in alcohols such as ethanol (10 mg/ml in absolute ethanol). Although water is the best solvent to provide a Vitamin C solution, it is paradoxically one of the worst to protect it against oxidative damages. The problem to be solved with ascorbic acid formulations has thus always been to find a compromise between solubilization and stability. Furthermore, because of its sensitivity, it can be a challenge to combine Vitamin C with certain active ingredients (such as polyamines), while maintaining adequate stability and activity of all components in the formulation. This is also true for many combinations of active ingredients.

For examples, because of their particular structure and related physicochemical properties, Vitamin C and polyamines (in particular 1,4-Diaminobutane or putrescine) are difficult to combine. For example, the addition of 1,4-DAB (strongly basic molecule; pka=10.8 at 20 degrees C; dissociation constant pK=10.8) affects the mechanism of action of Vitamin C (acidic molecule; pKa=4.7 at 10 degrees C; dissociation constant pK1=4.17; pK2=11.57) and its ability to penetrate the epidermis. Indeed, as an amine, salt and basic molecule, 1,4-DAB has a neutralization effect. It can react with L-Ascorbic acid (Vitamin C) to form a unitary structure and/or affect the pH of the final formulation, which in turn, can affect the activity and stability of Vitamin C and active ingredients in the formulation. It is thus a challenge to combine active ingredients having diverse properties (pKa's, dissociation constant, solubilities, etc.) such as 1,4-diaminobutane, Vitamin C and others while keeping them separate and in their active and bioavailable form. Furthermore, the designed formulation must remain stable for an extended period of time, which further adds to the difficulties of creating complex cosmetic compositions comprising multiple active ingredients of varying physico-chemical properties.

Thus, the creation of stable topical skin care compositions often presents many difficulties and challenges due to the nature of the active ingredients and unpredictable interactions between components in the final formulation. Another important challenge in the field of topical formulations (cosmetic and therapeutic) remains the ability to deliver active ingredients into the skin to reach target cells and provide biological effects. Factors that influence bioavailability and skin penetration of a given active ingredient are numerous and include size of the molecule, its lipophilic/hydrophilic nature, polarity, interactions with other components in the composition and skin condition.

Despite the number of solutions that have been proposed, there remains a need for novel skin care compositions and methods of use thereof.

SUMMARY OF THE INVENTION

Accordingly, the present invention provides new, skin care compositions which are stable and allow for the efficient penetration and delivery of active ingredients into the skin. These formulations may be used in therapeutic and cosmetic applications and are particularly useful in preventing and reducing skin's signs of aging, skin irritation and inflammation, promoting wound healing and thickening of the skin and/or reducing the development of scar tissue, including hypertrophic scar tissue.

In certain aspects compositions of the present invention stimulate the natural regenerating process of the skin, accelerate healing, promote new cell growth, increase healthy blood flow, even skin tone and boost collagen and moisture levels in the skin.

More specifically, compositions of the present invention contain multiple active ingredients (e.g., 5, 6, 7, 8, 9, 10, 11, 12, 13, 14, 15 or more) having various physicochemical properties and biological activities. In an aspect, the present invention provides complex stable compositions (e.g., eye, neck and body formulations) comprising primary polyamine (e.g., 1,4 diaminobutane) in combination with multiple additional active ingredients.

In an aspect, compositions of the present invention focus on reducing inflammation and rebalancing skin function, resulting in beautiful and optimized skin results. This is achieved through compositions of the present invention comprising multiple active ingredients including polyamines (e.g., 1,4 diaminobutane. Polyamine-DAB™) and other ingredients such as Vitamin-C (e.g., L-Ascorbic Acid USP, ascorbyl palmitate and 3-O-ethyl ascorbic acid), *Leontopodium alpinum Callus* culture extract, tocopheryl acetate, shea butter extract (*Butyrospermum parkii*), *Argania spinosa* Kernel oil, squalene, jojoba esters, *Pseudoalteromonas* ferment extracts, hydrolyzed wheat proteins, hydrolyzed soy proteins, hydrolyzed milk protein, tripeptide-1, tripeptide-10 citrulline, palmitoyl tripeptide-5, *Dunaliella Salina* extract, sodium hyaluronate, panthenol, retinol, cetyl palmitate, Di-C12-15 alkyl fumarate (Marrix™ U.S. Pat. No. 5,840,285), allyl methacrylates crosspolymer, butylated hydroxytoluene (BHT), glaucine (Bodyfit™ WO 2004/024695), acetylarginyltryptophyl diphenylglycine, collagen, sodium hyaluronate, and others.

In embodiments, compositions of the present invention contribute to strengthen the immune system; increase skin circulation, improve scar remodeling, repair DNA, replenish natural growth factors, re-establish the protective barrier, restore antioxidant levels, and activate collagen at the source to increase skin thickness.

In an aspect, the present invention provides a topical composition (water-based) comprising (i) a primary polyamine (e.g., putrescine/1,4 diaminobutane); (ii) at least one of Vitamin C, Vitamin E (alpha tocopherol), a jojoba ester or a peptide; and (iii) (a) at least one viscosity increasing agent/anticaking agent, (e.g., magnesium aluminum silicate); (b) at least one a binder/stabilizer (e.g., xanthan gum), (c) at least one skin conditioning agent (e.g., squalane); (d) at least one humectant, binder, emulsion stabilizer, surfactant and viscosity increasing agent (e.g., a blend of glyceryl stearate and PEG-100 stearate); (e) at least one rheology modifier (e.g., a blend of acrylates/acrylamide copolymer, mineral oil and polysorbate-85 (e.g., Novomer™ EC-1)); or (f) any combination of at least two of any one of (a) to (e).

Generally, water-based topical compositions described herein comprise between about 35% w/w and about 70% w/w of water. In embodiments, the water-based compositions comprise at least about 50% w/w water, preferably at least about 55% w/w and even more preferably at least about 60% w/w of water. In particular embodiments, the composition comprises between about 60% w/w and about 65% w/w of water.

In embodiments, the topical compositions described herein comprise at least one viscosity increasing agent/anticaking agent. In embodiments, the concentration of the at least one viscosity increasing agent/anticaking agent in compositions described herein is generally between about 0.6% w/w and about 3% w/w. In particular embodiments, the concentration of the at least one viscosity increasing agent/anticaking agent is between 0.8% w/w and 1.1% w/w. In embodiments, the viscosity increasing agent/anticaking agent comprises or consists of magnesium aluminum silicate.

In embodiments, the topical compositions described herein comprise at least one binder/stabilizer. In embodiments, the concentration of the at least one binder/stabilizer in compositions described herein is between about 0.1% w/w and about 0.9% w/w. In particular embodiments, the concentration of the at least one binder/stabilizer is between 0.1% w/w and 0.3% w/w. In embodiments, the binder/stabilizer is xanthan gum.

In embodiments, the topical compositions described herein comprise at least one skin conditioning agent. In embodiments, the concentration of the at least one skin conditioning agent in compositions described herein is between about 2% w/w and about 36% w/w. In particular embodiments, the concentration of the at least one skin conditioning agent is between about 2% w/w and about 7% w/w. In further particular embodiments, the concentration of the at least one skin conditioning agent is between about 4% w/w and 6% w/w. In embodiments, the at least one skin conditioning agent comprises or consists of squalane.

In embodiments, the topical compositions described herein comprise at least humectant, binder, emulsion stabilizer, surfactant and viscosity increasing agent. In embodiments, the concentration of the at least humectant, binder, emulsion stabilizer, surfactant and viscosity increasing agent in compositions described herein is between about 1% w/w and about 5% w/w. In particular embodiments, the concentration of the at least one humectant, binder, emulsion stabilizer, surfactant and viscosity increasing agent in compositions described herein is between about 1% w/w and about 5% w/w. In particular embodiments the concentration of the at least one at humectant, binder, emulsion stabilizer, surfactant and viscosity increasing agent in compositions described herein is between about 1% w/w and about 5% w/w. In particular embodiments the concentration of the at least one humectant, binder, emulsion stabilizer, surfactant and viscosity increasing agent in compositions described herein is between about 2.5% w/w and about 4.5% w/w. In embodiments, the at least one humectant, binder, emulsion stabilizer, surfactant and viscosity increasing agent comprises or consists of a blend of glyceryl stearate and PEG-100 stearate. In particular embodiments, the ratio of glyceryl stearate:PEG-100 stearate in the blend is between about 4:6 and about 6:4.

In embodiments, the topical compositions described herein comprise a rheology modifier. In embodiments, the concentration of the at least one rheology modifier in compositions described herein is between about 1% w/w and about 3% w/w. In particular embodiments, the concentration of the at least one rheology modifier is between about 1% w/w and about 1.5% w/w. In embodiments, the at least one rheology modifier comprises or consists of a blend of acrylates/acrylamide copolymer, mineral oil and polysorbate-85.

In embodiments, the topical compositions described herein further optionally comprise at least one stabilizer which improves wet and dry compatibility and water resistance. The concentration of such at least one stabilizer in compositions described herein is between about 0.5% w/w and about 5% w/w, preferably between about 1% w/w and about 5% w/w. In embodiments the concentration of such at least one stabilizer is between about 1% w/w and about 2% w/w. In embodiments, the at least one stabilizer is also a skin conditioning agent, emollient, moisturizer and/or solvent. In embodiments, the at least one stabilizer (conditioning agent, emollient, moisturizer and/or solvent) which improves wet and dry compatibility and water resistance comprises or consists of a blend of cyclopentasiloxane and dimethiconol.

In embodiments, compositions of the present invention further optionally comprise hexamidine diisethionate as an antifoaming, skin conditioning, emollient and/or preservative agent. The concentration of hexamidine diisethionate in compositions described herein is between about 0.09% w/w and about 0.9% w/w. In embodiments, the concentration of hexamidine diisethionate is about 0.1% w/w.

In embodiments, the above-noted primary polyamine in compositions described herein is a primary aliphatic lower-alkyl (C1-5) monoamine; a primary aliphatic alkylamine or a primary aliphatic lower-alkyl (C1-5) polyamine. In embodiments, the primary aliphatic lower-alkyl (C1-5) monoamine is aminoacetonitrile. In embodiments the primary aliphatic alkylamine is spermine or spermidine. In embodiments, the primary aliphatic lower-alkyl (C1-5) polyamine is putrescine or dansylcadaverine. In preferred embodiments, the primary aliphatic lower-alkyl (C1-5) polyamine is putrescine.

In embodiments, compositions of the present invention comprise between about 0.1% w/w and about 2% w/w of a primary polyamine. In embodiments, compositions of the present invention comprise between about 0.1% w/w and about 1% w/w of putrescine. In embodiments, about 0.4% w/w of putrescine. In other embodiments, about 0.8% w/w of putrescine.

In embodiments, compositions described herein comprise (in addition to a primary polyamine) at least one of Vitamin C, Vitamin E (alpha tocopherol), ajojoba ester or a peptide.

In embodiments, compositions of the present invention comprise Vitamin C. In embodiments, the Vitamin C comprises L-ascorbic acid, 3-O-ethyl ascorbic acid (ETVC), ascorbyl palmitate or a combination thereof. In other embodiments, the composition comprises a single form of Vitamin C (e.g., L-ascorbic acid, ascorbyl palmitate or 3-O-ethyl ascorbic acid). In particular embodiments, compositions of the present invention comprise more than zero and up to about 20% w/w of 3-O-ethyl ascorbic acid, ascorbyl palmitate, L-ascorbic acid or a combination thereof as Vitamin C. In embodiments, the compositions comprise about 10% w/w of L-ascorbic acid, ascorbyl palmitate and/or 3-O-ethyl ascorbic acid (ETVC). In embodiments, the compositions comprise about 0.05% w/w to about 0.5% w/w of L-ascorbic acid, ascorbyl palmitate and/or 3-O-ethyl ascorbic acid (ETVC).

In embodiments compositions of the present invention comprise Vitamin E. In embodiments, the Vitamin E comprises or consists of alpha tocopherol, gamma tocopherol and/or tocopheryl acetate. In embodiments, compositions of the present invention comprise between about 0.1% w/w and about 1% w/w of Vitamin E. In embodiments, about 0.3% w/w of Vitamin E.

In embodiments compositions of the present invention comprise a jojoba ester. In embodiments, compositions of the present invention comprise between about 0.1% w/w and about 1.5% w/w of jojoba ester. In embodiments, about 1% w/w of jojoba ester.

In embodiments compositions of the present invention comprise at least one peptide. In embodiments, the at least one peptide comprises or consists of (i) tripeptide 1, (ii) tripeptide 5, (iii) tripeptide 10 citrulline, (iv) tetrapeptide 2, (v) acetylarginyltryptophyl diphenylglycine or any combination of at least two of (i) to (v).

In a particular aspect, the present invention provides a composition comprising (in addition to a primary polyamine (e.g., putrescine)), *Leontopodium alpinum* extract (Majestem™, FR 3 031 454—WO 2016/113659). In an embodiment, the composition further comprises one or more of the following active ingredients: *Pseudoalteromonas* Ferment Extract, Hydrolyzed Wheat Protein, Hydrolyzed Soy Protein, Tripeptide-10 Citrulline, Tripeptide-1 (Trilagen™), shea butter, *Argania spinosa* kernel oil and squalane.

In a further particular aspect, the present invention provides a composition comprising in addition to a primary polyamine (e.g., putrescine), Vitamin C (e.g., L-Ascorbic Acid USP; ascorbyl palmitate and/or 3-O-ethyl ascorbic acid), retinol, *Leontopodium alpinum* extract (Majestem™, FR 3 031 454—WO 2016/113659) and a combination of Tripeptide-5, panthenol, sodium hyaluronate and algae extract (Syn-Eye™).

In a particular aspect, the composition comprising the above combination of ingredients is specifically designed for the delicate eye area to provide synergistic anti-wrinkle, anti-aging, anti-dark circle and firming actions. The specifically designed stable formulation allows avoiding or minimizing interactions between putrescine, Vitamin C, *Leontopodium alpinum* extract, Tripeptide-5 and other actives in the composition. In an embodiment, the composition further comprises one or more of shea butter, *Argania spinosa* kernel oil, squalene, *Pseudoalteromonas* Ferment Extract, Hydrolyzed Wheat Protein, Hydrolyzed Soy Protein, Tripeptide-10 Citrulline, Tripeptide-1 (Trilagen™) and Jojobas esters.

In yet a further aspect, the present invention provides a composition comprising, in addition to a primary polyamine (e.g., putrescine), (e.g., putrescine), Vitamin C (e.g., 3-O-ethyl ascorbic acid) *Leontopodium alpinum* extract (Majestem™, FR 3 031 454—WO 2016/113659), Acetyl Tetrapeptide-2 (Uplevity™), Pseudoalferomonas ferment extract, hydrolyzed wheat protein, hydrolyzed soy protein, Tripeptide-10 Citrulline, Tripeptide-1, (Trylagen™) Acetylarginyltryptophyl Diphenylglycine (Relistase™) and glaucine (Bodyfit™, WO 2004/024695). In an embodiment, the composition further comprises one or more of: comprises one or more of shea butter, *Argania spinosa* kernel oil and squalene.

In an embodiment, the composition comprising such combination of ingredients is specifically designed for the neck area for firming and tightening, fat-burning, anti-aging and moisturizing effects to reduce sagginess of the neck.

In embodiments, compositions of the present invention comprise one or more of the following carriers/diluents/excipients (non-active/inert ingredients): water, saline (0.9% sodium chloride solution) magnesium aluminum silicate, xanthan gum, triethanolamine, hexamidine diisethionate, Butylated Hydroxy Toluene (BHT), behenyl alcohol, glyceryl stearate, PEG-100 stearate, PEG-40 stearate, ceteareth-20, stearic acid, acrylates/acrylamide copolymer, mineral oil, polysorbate 85, hydroxypropylmethyl cellulose, glycerin, ethyl alcohol, butylene glycol, caprylyl glycol, coglucoside, cetearyl alcohol, glyceryl stearate, sodium stearoyl glutamate, dimethicone, dimethiconol, cellulose acetate propionate, propylene glycol stearate, SiCap™ 1500, ammonium acryloyldimethyltaurateNP copolymer, Aristoflex™ AVC, Novemer™ EC-1, Lipomulse™ luxe and mixtures thereof.

In particular embodiment, compositions of the present invention comprise one or more of the following carriers/diluents/excipients (non-active/inert ingredients): water, magnesium aluminum silicate, xanthan gum, triethanolamine, behenyl alcohol, glyceryl stearate, PEG-100 stearate, stearic acid, acrylates/acrylamide copolymer, mineral oil, polysorbate 85, Novemer™ EC-1 and mixtures thereof.

In embodiments, compositions of the present invention comprise one or more of the following carriers/diluents/excipients (non-active/inert ingredients): water, magnesium aluminum silicate, xanthan gum, triethanolamine, behenyl alcohol, glyceryl stearate, PEG-100 stearate, stearic acid, acrylates/acrylamide copolymer, mineral oil, polysorbate 85, allyl methacrylates crosspolymer, polysobate 20, Novemer™ EC-1 and mixtures thereof.

In embodiments, compositions of the present invention comprise one or more of the following carriers/diluents/excipients (non-active/inert ingredients): water, magnesium aluminum silicate, xanthan gum, triethanolamine, behenyl alcohol, hexamidine diisethionate, glycerin, glyceryl stearate, PEG-100 stearate, stearic acid, triethoxycaprilylsilane, castor oil, Lipomulse™ 165, dimethicone, acrylate acrylamide copolymer, mineral oil, polysorbate 85, Novemer™ EC-1 and mixtures thereof.

In embodiments compositions of the present invention further comprise, at least one antioxidant (in addition to or in place of Vitamin C) (tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, kinetin, wine extract, vitamin K, a plant extract, resorcinol, lactic acid and/or salicylic acid). In embodiments, the at least one antioxidant comprises a fruit extract, hydroquinone, vitamin E, resveratrol, a retinoid or any combination thereof. In embodiments, the at least one antioxidant comprises an antioxidant fruit extract. In embodiments, the compositions comprise between about 0.01% w/w and about 10% w/w of at least one antioxidant (in addition to Vitamin C). In embodiments, the compositions comprise about 1% w/w of at least one antioxidant.

In embodiments, the pH of compositions described herein is between about 6 and about 7.5, preferably between about 6.5 and 7.5. In embodiments, the pH of compositions described herein is between about 6.8 and about 7.5. In particular embodiments, the pH of compositions described herein is between about 7 and about 7.3. In particular embodiments, the pH of compositions described herein is about 6.8. In particular embodiments, the pH of compositions described herein is about 7.0. In particular embodiments, the pH of compositions described herein is about 7.3.

In embodiments, the above-noted compositions are (i) for treating or preventing skin inflammation, skin irritation, and/or skin's signs of aging; (ii) for promoting wound healing (iii) for preventing or reducing the formation of hypertrophic scar tissue; and/or (iv) for increasing for increasing skin's thickness.

In a related aspect, the present invention concerns the use of the above-noted topical composition (i) for treating or preventing skin inflammation, skin irritation, and/or skin's signs of aging; (ii) for promoting wound healing; (iii) for preventing or reducing the formation of hypertrophic scar tissue and/or (iv) for increasing skin's thickness.

In another aspect, the present invention concerns a process for preparing topical compositions described herein. In embodiments, the process comprises: (a) In a main tank: (ai) Combining water and the at least one viscosity increasing agent/anticaking agent; (aii) Adding to the mixture of (ai) the at least one binder/stabilizer; (aiii) Heating the mixture of (aii) to about 65-70 °C and mixing until obtaining an homogenous mixture; (b) in a separate tank, mixing (bi) the at least one humectant, binder, emulsion stabilizer, surfactant and viscosity increasing agent; (bii) squalane; and (biii) vitamin C, jojoba ester and/or vitamin E; heating to 65-70 °C and mixing until obtaining an homogenous mixture; (c) Adding the mixture of (b) to (a) and mixing until homogenization; (d) Cooling the mixture of (c) to about 50 °C; (e) Adding to (d) the rheology modifying agent and mixing until homogenization; (f) Cooling the mixture of (e) to about 40 °C; (g) In a separate tank, dissolving the primary polyamine (e.g., putrescine) in water (about 1% w/w to about 15% w/w, preferably about 5% w/w to about 15% w/w of water); and (h) Adding mixture of (g) to (f).

In another aspect, the present invention further concerns a process of preparing compositions described herein comprising: (a) In a main tank: (ai) Combining water and the at least one viscosity increasing agent/anticaking agent; (aii) Adding to the mixture of (ai) the at least one binder/stabilizer; (aiii) Heating the mixture of (aii) to about 65-70 °C and mixing until obtaining an homogenous mixture; (b) in a separate tank, mixing (bi) the at least one humectant, binder, emulsion stabilizer, surfactant and viscosity increasing agent; and (bii) squalane; heating to 65-70 °C; and mixing until obtaining an homogenous mixture; (c) Adding the mixture of (b) to (a) and mixing until homogenization; (d) Cooling the mixture of (c) to about 50 °C; (e) Adding to (d) the rheology modifying agent and mixing until homogenization; (f) Cooling the mixture of (e) to about 40 °C; (g) In a separate tank, dissolving putrescine in water (about 1-15% w/w, preferably about 5-15% w/w of water) and optionally add peptide; (h) Adding mixture of (g) to (f) and mixing until homogenization; (i) Adding Vitamin C to (h) under mixing.

In a further aspect the present invention concerns a process of preparing a composition described herein comprising: (a) In a main tank: (ai) Combining water and the at least one viscosity increasing agent/anticaking agent; (aii) Adding to the mixture of (ai) the at least one binder/stabilizer; (aiii) Heating the mixture of (aii) to about 65-70 °C and mixing until obtaining a homogenous mixture; (b) in a separate tank, mixing (bi) the at least one humectant, binder, emulsion stabilizer, surfactant and viscosity increasing agent; and (bii) squalane; heating to 65-70 °C; and mixing until obtaining an homogenous mixture; (c) Adding the mixture of (b) to (a) and mixing until homogenization; (d) Cooling the mixture of (c) to about 50 °C; (e) In a separate tank, combining water with hexamidine diisethionate (about 1% w/w to about 3% w/w water), heating to about 75-80 °C and mixing until dissolve and clear; (f) Adding to (d) at least one further stabilizer (e.g., cyclopentasiloxane and dimethiconol) and the rheology modifier; (g) In a separate container combining water (about 1% w/w to 5% w/w), Vitamin C, the primary polyamine (e.g., putrescine); heating to about 40 °C and mixing until homogenization; (h) Adding (g) to (f) under mixing at 40 °C; and (i) Combining (e) and (h) under mixing.

DESCRIPTION OF ILLUSTRATIVE EMBODIMENTS

Not all cosmetic products are alike. Important factors affecting cosmetic and therapeutic results include the stability of the active ingredient(s) in the compositions and their ability to penetrate the skin and reach its targeted layer(s) (e.g., the dermis and/or the epidermis). Applicants have developed new aqueous topical compositions comprising multiple active ingredients in which the active ingredients (e.g., putrescine and derivatives thereof, Vitamin C, retinol, etc.) i) are stable (i.e., do not react with each other and remain in their active form over a long period of time); and 2) efficiently penetrate the skin, thereby enabling the active ingredients to reach the cells and provide the desired effect.

In an aspect, the present invention provides a topical, water-based (aqueous) formulation comprising (i) at least one a primary polyamine; (ii) at least one further active ingredient (e.g., Vitamin C, Vitamin E (e.g., alpha or gamma tocopherol), a jojoba ester, a peptide, etc.); (iii) (a) at least one viscosity increasing agent/anticaking agent (e.g., magnesium aluminum silicate), (b) at least one a binder/stabilizer (e.g., xanthan gum); (c) at least one skin conditioning agent; (d) at least one humectant, binder, emulsion stabilizer, surfactant and/or viscosity increasing agent (e.g., a blend of glyceryl stearate and PEG-100 stearate); (e) at least one rheology modifier (e.g., a blend of acrylates/acrylamide copolymer, mineral oil and polysorbate-85 (e.g., Novomer™ EC-1); or (f) any combination of at least two of (a) to (e).

In embodiments, the active ingredient comprises Vitamin C (e.g., L-ascorbic acid, 3-O-ethyl ascorbate or acetyl palmitate).

The primary polyamines used in accordance with the present invention are preferably amine group terminated linear structures such as unbranched aliphatic compounds (e.g., lower C1-C10, preferably, C1-C5 alkyls). Such compounds include, but are not limited to naturally occurring putrescine (1,4-diaminobutane (Cas #333-93-7), H2N(CH2)4NH2), cadaverine (Cas #462-94-2, 1,5-pentanediamine, H2N(CH2)5NH2), spermidine (Cas #124-20-9, 1,4-butanediamine, N1-(3-aminopropyl, H2N(CH2)3NH(CH2)4NH2), spermine (Cas #71-44-3, 1,4-Butanediamine, N,N'-bis(3-aminopropyl), $H_2N(CH_2)_3NH(CH_2)_4$ $NH(CH_2)_3NH_2$) and their functional derivatives. The polyamines preferably have $(CH_2)_n$ groups linking nitrogen atoms where n is 2 to 10, preferably 2 to 6, more preferably 2 to 5 and particularly ones comprising 2 to 6 nitrogen atoms, particularly 2, 3 or 4 nitrogen atoms. These polyamines are available from natural sources, e.g. mammalian semen or fermentation products (for example from soy or anchovies), or may be manufactured by conventional techniques, e.g. solid-state polypeptide production followed by amidation and reduction. Polyamines useful in accordance with the present invention are described for example in WO2006/048671, U.S. Pat. No. 5,885,982 and CA 2,706,630. The polyamine(s) used in accordance with the invention may conveniently be in salt form with a physiologically tolerable counter ion, (e.g. inorganic/mineral acid, an organic acid such as an alpha-hydroxyacid or a fatty acid). Such salts, may be prepared by reaction of the polyamine and the acid, e.g. in solution for example in approximately equimolar amounts.

Under certain aspects, the total polyamine content in the compositions of the present invention is between about 0.0005 and about 5% w/w (e.g., between about 0.001% w/w and about 1% w/w, between about 0.005% w/w and about 1% w/w, between about 0.1% w/w and about 1% w/w). Preferably, in compositions for use in stimulating wound healing (e.g., reducing the appearance of scar tissue, including hypertrophic scar tissue), the concentration of putrescine is preferably between about 0.1% w/w and about 1% w/w, more preferably between about 0.4% w/w and about 0.8% w/w.

In certain aspects, compositions of the present invention comprise Vitamin C. As used herein, the term "Vitamin C" refers to ascorbic acid and its derivatives. Non-limiting examples of suitable forms of Vitamin C include: L-ascorbic acid, sodium ascorbyl phosphate (SAP), magnesium ascorbyl phosphate (MAP), ascorbyl palmitate (AA-PAL), ascorbyl tetra-isopalmitate (VC-IP), ascorbyl glucoside (AA-2G), ascorbyl 2-phosphate 6-palmitate (AAPS), 3-O-ethylascorbate (EAC), 3-O-ethyl ascorbic acid (e.g., ET-VC™). Preferably, compositions of the present invention comprise 3-O-ethyl ascorbic acid, ascorbyl palmitate (including magnesium and sodium ascorbyl palmitate) and/or L-ascorbic acid, more preferably, ethyl ascorbic acid and/or ascorbyl palmitate. In a preferred embodiment, a single form or source of Vitamin C is included in compositions of the present invention.

Under certain aspects, the concentration of Vitamin C in compositions of the present invention is between about 0.01% w/w and about 20% w/w. In embodiments, compositions of the present invention comprise at least 0.05% w/w, at least 0.5% w/w, at least 8% w/w, or at least 20% w/w of Vitamin C. In embodiments, the concentration of Vitamin C is about 0.05 w/w, 0.5% w/w, about 1% w/w, about 5% w/w, about 10% w/w, about 12% w/w, about 12.5% w/w, about 8% w/w, about 15% w/w, about 16% w/w, about 18% w/w, or about 20% w/w.

Compositions of the present invention comprise, in addition to putrescine, multiple active ingredients (e.g., useful for reducing or preventing skin aging, skin irritation and inflammation, for improving skin texture, skin tone and/or skin healing). Actives are defined as skin benefit agents other than emollients and ingredients that merely improve the physical characteristics of the composition.

Non-limiting examples of active ingredients that may be added in compositions of the present invention include: retinol, lactic acid, kojic acid, proanthocyanamide, proanthocyanidins, wine extract, *Pseudoalteromonas* ferment extract, squalane, Di-C12-15-alkyl fumarate (U.S. Pat. No. 5,840,285), castor oil, hydrolyzed wheat protein, hydrolyzed soy protein, *Glycine soja* (soybean) protein, citrulline, tripeptide-1 (glycine,-histidine-lysine), tripeptide-5, palmitoyl tripeptide-5, tripeptide-8, tripeptide-10, glycine, *Butyrospermum parkii* (shea) butter, *Argania spinosa* kernel oil, jojoba esters, glaucine, acetyl tetrapeptide-2, tetrapeptide 21, *Leontopodium alpinum Callus* culture extract, acetylarginyltryptophyl diphenylglycine, *Carapa guaianensis* seed oil, glucose, hydrolyzed rice protein, superoxide dismutase, *Rosmarinus officinalis* (rosemary) leaf extract, cetearyl olivate, sorbitan olivate, *Ruscus aculeatus* root extract, *Centella asiatica* extract, hydrolyzed yeast protein, hydrolyzed casein, *Calendula officinalis* flower extract, *Dunaliella Salina* extract, Acacia Senegal gum, *Crocus chrysanthus* bulb extract, *Opuntia ficus-indica* stem cell extract, bulbine frutescens leaf juice, *Symphytum Officinale Callus* culture extract, acetyl hexapeptide-3, allantoin, *Citrus grandis* (grapefruit) extract, hydrolyzed glycosaminoglycans, hyaluronic acid, acetylated hyaluronic acid, sodium hyaluronate, hydrolised sodium hyaluronate, *Persea gratissima* (avocado) oil, tropolone, lysine hcl, *Porphyridium cruentum* extract, dimethiconol, caprylic/capric triglyceride, Cytokinol™, phytonadione (Vitamin K), Vitamin E (tocopherols (e.g., γ-tocopherol, alpha-tocopherol) and tocotrienols), phloretin, ferulic acid (e.g., in combination with vitamin C), escin, panthenol, hexylresorcinol, Argireline, Kinetin, CE ferulic Acid, skin growth factors, Petrolatum/Canolin, dimethyl sulphoxide, coconut oil, keratolytic agents, unsaturated fatty acids (e.g. omega-3, omega-6 and omega-9 unsaturated fatty acids, especially omega-3 acids, for example EPA, DHA and ALA) and derivatives (particularly esters) thereof, HMG-CoA reductase inhibitors, natural triterpenes, Coenzyme Q10 (ubiquinone), vitamin B3, hydroquinone (tocopheryl acetate), glycerine, ethyl linoleate, resveratrol, hydroxyresveratrol, Polyglyceryl-10 Oleate. Aloe, *Mallotus japonicus* extract, hydroxyacids (e.g. alpha hydroxy acids such as glycolic acid, beta hydroxyl acids such as salicylic acid), beta-(1,3) glucans, extract of unpolished rice, urea, pine seed oil, marine collagens, soluble collagen, plant cell extracts, ceramides (NP, NS, EOS, EOP, AP), Caprooyl Phytosphingosine, Caprooyl Sphingosine, cholesterol, glutathione, carnitine, caffeine, *Rosa mosqueta* oil, cysteine derivatives, acid and alpha-amino acids, and salts of any of these.

In embodiments, compositions of the present invention comprise one or more antioxidants. As used herein, the term "antioxidant" refers to compounds, natural or synthetic, capable of neutralizing reactive oxygen species (ROS). Commonly used antioxidants in compositions (dermatological compositions) include, for example, ascorbic acid (Vitamin C and derivatives thereof), tocopherol (Vitamin E and derivatives thereof), isoflavones, polyphenols, and retinoids, (including retinoic acid (0.25% to 0.1%), tretinoin, retinal, retinol (0.1% to 5%), Adapalene, tazorotene and retinyl esters. (Reviewed in Sheri L. Rolewski. Dermatology Nursing. 2003; 15(5), Jannetti Publications, Inc.), alpha lipoic acid, beta-glucan, coenzyme Q10, grape seed extract, amino acids, green tea, soybean sterols, ergothioneine (EGT, a thiourea derivative of histidine), Resorcinol, Carcinine, butylated hydroxytoluene, butylated hydroxyanisole, astaxanthin, alpha lipoic acid, tocotrienols and mixtures thereof. In embodiments, compositions of the present invention comprise Vitamin C and at least one further antioxidant. In embodiments, compositions of the present invention further comprise (in addition to putrescine and/or Vitamin C) one or more of the following active ingredients: an antioxidant (e.g., a retinoid such as retinol or retinyl palmitate), grapefruit extract, resveratrol, Vitamin E and/or hydroquinone. Generally, the concentration of retinoids (such as retinol) that may be used in accordance with the present invention is between about 0.01% w/w and about 10% w/w, preferably between about 0.01% w/w and about 5% w/w.

Generally, the total amount of active ingredients in compositions of the present invention may be up to 40% w/w of the composition. In embodiments, the total amount of active ingredients in compositions of the present invention is between about 0.4% w/w and about 35% w/w. In embodiments, the total amount of active ingredients is between about 0.4% w/w and about 30% w/w. In embodiments, the total amount of active ingredients is up to 25% w/w of the composition. In embodiments, the total amount of active ingredients is up to 20% w/w of the composition. In embodiments, the total amount of active ingredients in compositions of the present invention is between about 1% w/w and about 17% w/w.

The compositions according to the invention may be in any form suitable for topical application, e.g. creams, lotions, ointments, gels, balm, solutions, emulsions, dispersions, suspensions etc. and may if desired include a carrier substrate, e.g. a woven or nonwoven web. The compositions may contain conventional topical composition components, such as for example, solvents, oils (e.g. plant oils), aromas, sunscreens, colorants, pH modifiers, viscosity modifiers, binders, diluents, emollients, skin irritants, thickeners, preservatives, stabilizers, humidifiers, skin penetration enhancers, vesicle wall formers, etc. Preferably, compositions of the present invention are topical serums, lotions, creams and ointments.

Sunscreens include those materials commonly employed to block ultra-violet radiation. Illustrative compounds are the derivatives of para-aminobenzoic acid (PABA), cinnamate and salicylate. For example, avobenzophenone (Parsol 1789®) octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX™, Parsol HS and Benzophenone-3™, respectively. The exact amount of sunscreen employed in the compositions can vary depending upon the degree of protection desired from the sun's ultra-violet radiation. Additives that reflect or scatter the sun rays may also be employed. These additives include oxides like zinc oxide and titanium dioxide.

Non-limiting examples of conventional topical composition components that may be included in compositions of the present invention include: lecithin, xanthan gum, carbomer, triethanolamine, phenoxyethanol, butylene glycol, caprylyl glycol, glyceryl stearate, PEG-100 stearate, PEG-75 stearate, PEG 40, dimethicone, glycerin, behenyl alcohol, behenic acid, cetyl palmitate, cyclopentasiloxane, dimethiconol, acrylates/acrylamide copolymer, magnesium aluminum silicate, methylparaben, ethylparaben, propylparaben, butylparaben, stearic acid, caprylic/capric triglyceride, titanium dioxide, triethoxycaprylylsilane, castor oil phosphate, tocopheryl acetate, tetrasodium edta, butylated hydroxy toluene, allyl methacrylates crosspolymer, polysorbate 20, carrageenan (*Chondrus crispus*), ethylhexylglycerin, cetyl alcohol, ceteareth-20, ceteareth-25, ceterayl alcohol, steareth-20, pentylene glycol, sodium benzoate, sodium dextran sulfate, potassium sorbate, ammonium glycyrrhizate, ethoxydiglycol, propylene glycol, propylene glycol stearate, betaine, saccharide isomerate, trimethylolpropane, tricaprylate/tricaprate, cetyl alcohol, dmdm hydantoin, isobutylparaben, 1,2-hexanediol, 1,2-octanediol, hydrogenated palm glycerides, glyceryl polyacrylate, mineral oil, allyl methacrylate crosspolymer, polysorbate-85, glyceryl dilaurate, C13-14 isoparaffin, laureth-7, C12-13 pareth-23, Hexamidine Diisethionate, Petrolatum and derivatives, Benzoyl Peroxide, lanolin, isomalt, hydroxypropyl methylcellulose, Ammonium acryloyldimethyltaurateNP copolymer, Aristoflex™ AVC, Novemer™ EC-1, Lipomulse™ 165, Lipomulse™ luxe and SiCap™ 1500.

Many compositions, especially those containing water, may be protected against the growth of potentially harmful microorganisms. Anti-microbial compounds and preservatives are, therefore, typically incorporated into such compositions. Suitable preservatives include alkyl esters of p-hydroxybenzoic acid (parabens), hydantoin derivatives, propionate salts, parabens and a variety of quaternary ammonium compounds as well as chelating agents such as EDTA and well known non-parabens antimicrobial of all kinds.

TABLE 1

Exemplary concentrations of excipients that may be included in the compositions of the present invention.

| Excipient | Concentration range (% w/w) | Excipient | Concentration range (% w/w) |
|---|---|---|---|
| Water | 35% to 70% | Butylene glycol | 0.00002-1% |
| Magnesium aluminum silicate | 0.6 to 3.0% | Polysorbate 20 | 0.001-0.3% |
| Xanthan gum | 0.1 to 0.9% | Lecithin | 0.00002-1% |
| Triethanolamine | 0.0002 to 6% | Carbomer | 0.00002-1% |
| hexamidine diisethionate | 0.09 to 0.9% | Hydroxypropylmethyl cellulose | 0.1 to 1% |
| Behenyl alcohol | 0.2 to 3% | Glycerin | 1.0 to 4.0% |
| Cetyl alcohol | 0.2 to 3% | Cetearyl alcohol | 1-5% |
| Glyceryl stearate | 1 to 5% | Ceteareth-20 | 1-5% |
| PEG-100 stearate | 1 to 4% | Ceteareth-25 | 1-5% |
| PEG-40 stearate | 1 to 5% | Sodium stearoyl glutamate | 1-5% |
| Stearic acid | 0.0005-5% | Dimethicone | 1-15% |
| triethoxycaprilylsilane | 1.0 to 2% | Dimethiconol | 1-5% |
| Castor oil phosphate | 0.002-10% | Novemer ™ EC-1 | 1-3% |
| Acrylates/acrylamide copolymer | 1-2% | Lipomulse ™ 165 | 0.1-5% |
| Mineral oil | 1-3% | Lipomulse ™ luxe | 1-5% |
| | | Butylated Hydroxy Toluene (BHT) | 0.008-0.1% |
| Polysorbate 85 | 1-3% | Carpylyl glycol | 0.00002-1% |
| Allyl methacrylate cross polymer | 0.008-0.1% | | |

Compositions of the present invention are water based (aqueous) formulations preferably having a neutral or acidic pH (i.e., 7.5 or below, generally between 6.8 and 7.5. Compositions comprising putrescine should have a pH below its pKa (which is 10.51). The water content of compositions of the present invention is generally between 35% and 70%.

Uses

Compositions of the present invention are intended to be used as is, or through the making of a composition or a medication, to prevent or to treat any skin condition that involves or is caused by ROS or involving collagen synthesis or transglutaminase activity. The skin condition includes but is not limited to skin irritation or inflammation, dermatitis, skin allergy, psoriasis, acne, eczema, rosacea, radiations exposure including U.V. or sun exposure, laser exposure, skin aging (e.g., reduction of wrinkles), dry skin, skin surgery and wound healing. Compositions comprising putrescine and preferably putrescine and Vitamin C are particularly useful for promoting wound healing, reducing and/or preventing skin's signs of ageing (e.g., increasing skin's thickness and hyperpigmentation), skin inflammation and/or skin irritation and preventing and/or treating scars including hypertrophic scar tissue.

General Manufacturing Procedures

Compositions of the invention may be produced by standard cosmetic or pharmaceutical composition production techniques.

However, the processes described in Examples 1-3 have been found particularly useful in preparing compositions of the present invention.

All steps, except the heating step, if required, are performed at room temperature (about 18-25 °C).

These order/sequence of the various steps in the processes help to dissolve high amounts of active ingredients, avoid unwanted reaction between active ingredients and formulate stable, homogeneous topical compositions.

For compositions comprising putrescine, the putrescine is preferably added near or at the end of the process, after Vitamin C and other ingredients have been added, when the process no longer requires heating and the solution is at about 40 degrees Celsius or cooler.

The selection of the right solvents/excipients and of the right sequential addition of putrescine, other active ingredients (e.g., Vitamin C, Vitamin E, jojoba ester and/or peptide (s)) and excipients, combined to a high speed that allows micronization of active ingredients into such a solution, all contribute to obtaining a complex, yet stable formulation comprising multiple active ingredients. A micronization process appears to result in a product wherein the interaction between putrescine and reacting ingredient (e.g., Vitamin C, Vitamin E, jojoba ester, peptide(s)) is reduced. The process also decreases the contact of oxygen with sensitive active ingredients (e.g., Vitamin C) once in solution and therefore reduces the oxidative damages to active components in the formulation. These features provide for unique stable formulations with extensive cosmetic action.

More specifically, the present invention provides the following items:

1. An aqueous topical composition comprising (i) a primary polyamine; (ii) at least one of Vitamin C, Vitamin E (alpha tocopherol), a jojoba ester or a peptide; and (iii) (a) at least one viscosity increasing agent/anticaking agent, (b) at least one a binder/stabilizer; (c) at least one skin conditioning agent; (d) at least one humectant, binder, emulsion stabilizer, surfactant and viscosity increasing agent; (e) at least one rheology modifier; or (f) any combination of at least two of any one of (a) to (e).

2. The topical composition of item 1, wherein said primary polyamine is a primary aliphatic lower-alkyl (C1-5) monoamine; a primary aliphatic alkylamine or a primary aliphatic lower-alkyl (C1-5) polyamine.

3. The topical composition of item 2, wherein said primary aliphatic lower-alkyl (C1-5) monoamine is aminoacetonitrile, said primary aliphatic alkylamine is spermine or spermidine and said primary aliphatic lower-alkyl (C1-5) polyamine is putrescine or dansylcadaverine.

4. The topical composition of item 3, comprising putrescine.

5. The topical composition of item 4, comprising between about 0.1% w/w and about 2% w/w of putrescine.

6. The topical composition of item 4, comprising about 0.4% w/w of putrescine.

7. The topical composition of item 4, comprising about 0.8% w/w of putrescine.

8. The topical composition of any one of items 1 to 7, comprising Vitamin C, wherein the Vitamin C consists of L-ascorbic acid, 3-O-ethyl ascorbic acid (ETVC), ascorbyl palmitate or any combination of at least two thereof.

9. The topical composition of any one of items 1 to 8, comprising between about 0.05% w/w and about 20% w/w of Vitamin C.

10. The topical composition of any one of items 1 to 9, comprising Vitamin E.

11. The topical composition of 10, comprising between about 0.1% w/w and about 1% w/w of Vitamin E.

12. The topical composition of 11, comprising about 0.3% w/w of Vitamin E.

13. The topical composition of any one of items 1 to 12, comprising a jojoba ester.

14. The topical composition of 13, comprising between about 0.1% w/w and about 1.5% w/w of a jojoba ester.

15. The topical composition of 14, comprising about 1% of a jojoba ester.

16. The topical composition of any one of items 1 to 15, comprising at least one peptide.

17. The topical composition of item 16, wherein the at least one peptide is (i) tripeptide 1, (ii) tripeptide 5, (iii) tripeptide 10 citrulline, (iv) tetrapeptide 2, (v) acetylarginyltryptophyl diphenylglycine or any combination of at least two of any one of (i) to (v).

18. The topical composition of any one of items 1 to 17, comprising at least one viscosity increasing agent/anticaking agent, wherein the concentration of the at least one viscosity increasing agent/anticaking agent is between about 0.6% w/w and about 3% w/w.

19. The topical composition of any one of items 1 to 18, comprising at least one viscosity increasing agent/anticaking agent, wherein the at least one viscosity increasing agent/anticaking agent is magnesium aluminum silicate.

20. The topical composition of any one of items 1 to 19, comprising at least one binder/stabilizer, wherein the concentration of the at least one binder/stabilizer is between about 0.1% w/w and about 0.9% w/w.

21. The topical composition of any one of items 1 to 20, comprising at least one binder/stabilizer, wherein the at least one binder/stabilizer is xanthan gum.

22. The topical composition of any one of items 1 to 21, comprising at least one skin conditioning agent, wherein the concentration of the at least one skin conditioning agent is between about 2% w/w and about 36% w/w.

23. The topical composition of any one of items 1 to 22, comprising at least one skin conditioning agent, wherein the at least one skin conditioning agent is squalane.

24. The topical composition of any one of items 1 to 23, comprising at least one at least one humectant, binder, emulsion stabilizer, surfactant and viscosity increasing agent, wherein the concentration of the at least one at least one humectant, binder, emulsion stabilizer, surfactant and viscosity increasing agent is between about 1% w/w and about 5% w/w.

25. The topical composition of any one of items 1 to 24, comprising at least one humectant, binder, emulsion stabilizer, surfactant and viscosity increasing agent, wherein the at least one at least one humectant, binder, emulsion stabilizer, surfactant and viscosity increasing agent is a blend of glyceryl stearate and PEG-100 stearate in a ratio of between about 4:6 and about 6:4 of glyceryl stearate: PEG-100 stearate.

26. The topical composition of any one of items 1 to 25, comprising at least one at least one rheology modifier, wherein the concentration of the at least one rheology modifier is between about 1% w/w and 3% w/w.

27. The topical composition of any one of items 1 to 26, comprising at least one at least one rheology modifier, wherein the at least one rheology modifier is a blend of acrylates/acrylamide copolymer, mineral oil and polysorbate-85.

28. The topical composition of any one of items 1 to 27, further comprising at least one stabilizer which improves wet and dry compatibility and water resistance, wherein the concentration of the at least one stabilizer is between about 1% w/w and about 5% w/w.

29. The topical composition of item 28, wherein the at least one stabilizer is also a skin conditioning agent, emollient; moisturizer and solvent.

30. The topical composition of item 29, wherein the at least one stabilizer which improves wet and dry compatibility and water resistance is a blend of cyclopentasiloxane and dimethiconol.

31. The topical composition of any one of items 1 to 30, further comprising hexamidine diisethionate as an antifoaming, skin conditioning, emollient and preservative agent.

32. The topical composition of item 31, comprising about 0.1% w/w hexamidine diisethionate.

33. The topical composition of any one of items 1 to 32, further comprising at least one antioxidant.

34. The topical composition of item 33, wherein at least one antioxidant comprises a fruit extract, hydroquinone, a retinoid, resveratrol, tocopherol, tocopheryl acetate, retinol, retinyl palmitate, hydroquinone, proanthocyanidins, butylated hydroxytoluene, butylated hydroxyanisole, astaxanthin, alpha lipoic acid, tocotrienols, coenzyme Q10, α-hydroxy acid, kojic acid, kinetin, wine extract, vitamin K, a plant extract, resorcinol, lactic acid, salicylic acid or any combination of at least two thereof.

35. The topical composition of any one of items 1 to 34, wherein the pH of the composition is between about 6.5 and about 7.5.

36. The topical composition of any one of items 1 to 35, comprising at least 5 active ingredients.

37. The topical composition of any one of items 1 to 35, comprising at least 10 active ingredients.

38. The topical composition of any one of items 1 to 35, comprising at least 12 active ingredients.

39. The topical composition of any one of items 1 to 38, comprising between about 55% and 65% w/w of water.

40. The topical composition of any one of items 1 to 39, for treating or preventing skin inflammation, skin irritation, and/or skin's signs of aging; and/or for increasing skin thickness.

41. The topical composition of any one of items 1 to 39, for promoting wound healing.

42. The topical composition of any one of items 1 to 39, for preventing or reducing the formation of hypertrophic scar tissue.

43. Use of the topical composition defined in any one of items 1 to 39, for treating or preventing skin inflammation, skin irritation, and/or skin's signs of aging; and/or for increasing skin thickness.

44. Use of the topical composition defined in any one of items 1 to 39, for promoting wound healing.

45. Use of the topical composition defined in any one of items 1 to 39, for preventing or reducing the formation of hypertrophic scar tissue.

46. A process of preparing the composition defined in any one of items 1 to 39, comprising:

(a) in a main tank:
  (ai) combining water and the at least one viscosity increasing agent/anticaking agent;
  (aii) adding to the resulting mixture of (ai) the at least one binder/stabilizer;
  (aiii) heating the resulting mixture of (aii) to about 65-70 °C and mixing until obtaining an homogenous mixture;
(b) in a separate tank, mixing
  (bi) the at least one humectant, binder, emulsion stabilizer, surfactant and viscosity increasing agent;
  (bii) squalane; and
  (biii) vitamin C, jojoba ester and/or vitamin E; and heating to 65-70 °C and mixing until obtaining an homogenous mixture;
(c) adding the resulting mixture of (b) to (a) and mixing until homogenization;
(d) cooling the resulting mixture of (c) to about 50 °C;
(e) adding to (d) the rheology modifying agent and mixing until homogenization;
(f) cooling the resulting mixture of (e) to about 40 °C;
(g) in a separate tank, dissolving the primary polyamine (e.g., putrescine) in water (about 1-15% w/w, preferably about 5-15% w/w of water); and
(h) adding the resulting mixture of (g) to the resulting mixture of (f).

47. A process of preparing the composition defined in any one of items 1 to 39, comprising:

(a) in a main tank:
  (ai) combining water and the at least one viscosity increasing agent/anticaking agent;
  (aii) adding to the resulting mixture of (ai) the at least one binder/stabilizer;
  (aiii) heating the resulting mixture of (aii) to about 65-70 °C and mixing until obtaining an homogenous mixture;
(b) in a separate tank, mixing (bi) the at least one humectant, binder, emulsion stabilizer, surfactant and viscosity increasing agent; and (bii) squalane; heating to 65-70 °C; and mixing until obtaining an homogenous mixture;
(c) adding the resulting mixture of (b) to the resulting mixture of (a) and mixing until homogenization;
(d) cooling the resulting mixture of (c) to about 50 °C;
(e) adding the rheology modifying agent to the resulting mixture of (d) and mixing until homogenization;
(f) cooling the resulting mixture of (e) to about 40 °C;
(g) in a separate tank, dissolving putrescine in water (about 1-15% w/w, preferably about 5-15% w/w of water) and optionally adding a peptide;
(h) adding the resulting mixture of (g) to the resulting mixture of (f) and mixing until homogenization; and
(i) adding Vitamin C to the resulting mixture of (h) under mixing.

48. A process of preparing the composition defined any one of items 31 to 39, comprising:

(a) in a main tank:
  (ai) combining water and the at least one viscosity increasing agent/anticaking agent;
  (aii) adding to the resulting mixture of (ai) the at least one binder/stabilizer;
  (aiii) heating the resulting mixture of (aii) to about 65-70 °C and mixing until obtaining a homogenous mixture;
(b) in a separate tank, mixing (bi) the at least one humectant, binder, emulsion stabilizer, surfactant and viscosity increasing agent; and (bii) squalane; heating to 65-70 °C; and mixing until obtaining an homogenous mixture;
(c) adding the resulting mixture of (b) to the resulting mixture of (a) and mixing until homogenization; (d) cooling the resulting mixture of (c) to about 50 °C;
(e) in a separate tank, combining water with hexamidine diisethionate (about 1% w/w to about 3% w/w water), heating to about 75-80 °C and mixing until dissolved and clear;
(f) adding to the resulting mixture of (d) at least one further stabilizer (e.g., cyclopentasiloxane and dimethiconol) and the rheology modifier;

(g) in a separate container combining water (about 1% w/w to 5% w/w), Vitamin C, the primary polyamine (e.g., putrescine); heating to about 40 °C and mixing until homogenization;

(h) adding the resulting mixture of (g) to the resulting mixture of (f) under mixing at 40 °C; and (j) combining the resulting mixture of (e) and the resulting mixture of (h) under mixing.

Other objects, advantages and features of the present invention will become more apparent upon reading the following non-restrictive description of specific embodiments thereof, given by way of example only with reference to the accompanying drawings.

The present invention is illustrated in further details by the following non-limiting examples.

Example 1

Complex Eye Cream Comprising Multiple Active Ingredients Including Putrescine and Vitamin C

TABLE 2

Exemplary 0.4% putrescine and Vitamin C (0.05%) eye cream

| | Ingredients (INCI Name) | Function(s) | Ingredients (Trade Name and Manufacturer) | CAS# | Grade | Amount (% W/W) |
|---|---|---|---|---|---|---|
| | | | Part A | | | |
| 1 | Water | Diluent/carrier | Purified Water | N/A | USP | 58.80 |
| 2 | Magnesium Aluminum Silicate | Viscosity increasing agent; Absorbent; Anticaking agent; Opacifying agent; Slip modifier | Veegum Ultra; RT Vanderbilt | 12199-37-0, 13463-67-7, 14808-60-7 | MFR | 0.90 |
| 3 | Xanthan Gum | Binder; Emulsion Stabilizer (gel forming); Skin conditioning agent; Surfactant - Emulsifying agent; Viscosity increasing agent | Jungbunzlauer Xanthan Gum; Pachem Distribution | 11138-66-2 | MFR | 0.20 |
| 4 | Phenoxyethanol (69-72%), Methylparaben (15-17%), Ethylparaben (3.5-4.5%), Propylparaben (1.7-2.3%), Butylparaben (5.5-6.5%) (about 29% parabens in total) | Broad spectrum preservative (inhibits the growth of gram (+) and gram (−) bacteria, yeasts and molds) | Lincocide P-MEPB; Lincoln fine Ingredients | 122-99-6, 99-76-3, 94-26-8, 94-13-3, 120-47-8 | MFR | 0.60 |
| 5 | Triethanolamine | Surfactant and pH adjusting chemical (buffer); Emulsifying agent | Triethanolamine; Canada Colors and Chemicals | 102-71-6 | MFR | 0.25 |
| 6 | TetraSodium EDTA | Chelating agent | Versene 220; Canada Colors and Chemicals | 8013-51-2 | MFR | 0.10 |
| | | | Part B | | | |
| 7 | Behenyl Alcohol | Binder; Emollient, Emulsifier and Viscosity increasing agent (thickener). | Lanette 22; Pachem Distribution (BASF) | 661-19-8 | MFR | 1.50 |
| 8 | Cetyl Palmitate | Skin-conditioning agent - Emollient; Occlusive | Trivent CP; Alzo International | 540-10-3 | MFR | 1.50 |
| 9 | Glyceryl Stearate (40-60%), PEG-100 Stearate (40-60%) | Humectants, solvents, binders, surfactant, emulsion stabilizers, and viscosity increasing agents | Lipomulse 165; Tempo Canada | 123-94-4, 9004-99-3 | MFR | 4.00 |
| 10 | Stearic Acid | Surfactant; Emulsifying agent; refatting | Stearic Acid; Univar | 57-11-4 | MFR | 0.50 |
| 11 | Tocopheryl Acetate | Active ingredient, Antioxidant; Skin-conditioning agent | Vitamin E; Pachem Distribution (BASF) | 7695-91-2 | MFR | 0.30 |
| 12 | Butylated Hydroxy Toluene | Preservative; antioxidant | BHT; Andicor Specialty Chemicals (Evonik) | 128-37-0 | MFR | 0.10 |
| 13 | Butyrospermum Parkii (Shea) Butter Extract | Active ingredient: Skin-conditioning | Cetiol SB-45/Fancol Shea Butter; Pachem (Cognis)/Unipex Solution (Elementis) | 68920-03-6 | MFR | 2.00 |
| 14 | Dimethicone | Lubricant and skin conditioning agent; occlusive; skin protectant; emollient | DC 200/350/Elements PDMS 350; Canada Colors and Chemicals (Momentive) | 9006-65-9 or 63148-62-9 | MFR | 2.00 |
| 15 | Argania Spinosa Kernel Oil | Active ingredient: Skin conditioning agent - Emollient; Occlusive | Argan Oil; Centerchem (DSM) | 223747-87-3 | MFR | 1.00 |
| 16 | Squalane | Active ingredient: Lubricant on the skin surface. Skin conditioning agent with refatting properties - occlusive; emollient; refatting | Keteol V; Pachem Distribution | 111-01-3 | MFR | 5.00 |
| 17 | Ascorbyl Palmitate (Vit C) | Active ingredient: Antioxidant, and wound healing agent. Increases collagen production and reduce the inflammation. | Ascorbyl Palmitate; Spectrum Chemicals (VWR International)/ Green Wave Ingredients | 137-66-6 | MFR | 0.05 |

TABLE 2-continued

Exemplary 0.4% putrescine and Vitamin C (0.05%) eye cream

| | Ingredients (INCI Name) | Function(s) | Ingredients (Trade Name and Manufacturer) | CAS# | Grade | Amount (% W/W) |
|---|---|---|---|---|---|---|
| 18 | Caprylic/Capric Triglyceride, Titanium Dioxide, Triethoxycaprylylsilane, Castor Oil Phosphate | Caprylic/Capric Triglyceride: Fragrance Ingredient, Skin conditioning agent-Occlusive<br>Titanium dioxide: Colorant; Opacifying agent; Sunscreen agent; Ultraviolet Light Absorber<br>Triethoxycaprylylsilane: Binder<br>Castor Oil Phosphate: Anticaking agent, emulsion stabilizer | 50% Ultrafine $TiO_2$ in Caprylic/Capric Triglyceride Dispersion (R3214, Sensient- Product discontinued and replaced by Sensient Covascreen ™ UVR CCT product code: 251351). | 65381-09-1, 13463-67-7, 2943-75-1, 68308-61-2 | MFR | 0.50 |
| 19 | Jojoba Esters Derived from jojoba oil (*Simmondsia chinensis*) Blend of 99.95% Jojoba Esters and 0.05% tocopherol | Active ingredient: Skin conditioning and anti-aging: Improves skin barrier function (occlusive); Increase skin's hydration; reduces skin dryness, roughness and flakiness. Also reduces peri-ocular fine-line wrinkles and increases skin firmness | Floraesters ™ 30; Vivachem (Floratech) | 61789-91-1 | MFR | 1.00 |
| 20 | Phenoxyethanol (69-72%), Methylparaben (15-17%), Ethylparaben (3.5-4.5%), Propylparaben (1.7-2.3%), Butylparaben (5.5-6.5%) (about 29% parabens in total) | Broad spectrum preservative (inhibits the growth of gram (+) and gram (−) bacteria, yeasts and molds) | Lincocide ™ P-MEPB; Lincoln fine Ingredients | 122-99-6, 99-76-3, 94-26-8, 94-13-3, 120-47-8 | MFR | 0.30 |
| | | | Part C | | | |
| 21 | Acrylates/Acrylamide Copolymer (about 26-28%), Mineral Oil (about 22-24%), and Polysorbate 85 (1-3%), water (up to 100% i.e., 45-51%) | Emulsifier; rheology modifier; 27% solids, liquid, pre-neutralized polymer dispersed in oil. It is a multifunctional polymer used in emulsions containing active ingredients with electrolytes and suspended inorganic pigments. | Novemer ™ EC-1; LV Lomas (Lubrizol) | N/A, 8042-47-5, 9005-70-3 | MFR | 1.50 |
| 22 | Cyclopentasiloxane, Dimethiconol | Skin conditioning agent - Emollient; Moisturizer; Solvent. Improves wet and dry compatibility. Exhibits improved skin feel and water resistance. Provides smooth but not greasy feel. Possesses non- fatty and non-sticky properties | Abil ™ OSW-5; Andicor Specialty Chemicals (Evonik) | 541-02-6, 31692-79-2 | MFR | 1.50 |
| | | | Part D | | | |
| 23 | Water | Diluent/carrier | Purified Water | N/A | USP | 5.00 |
| 24 | 1,4-Diaminobutane Dihydrochloride (putrescine) | Active ingredient: Skin regeneration. Promotes skin repair including wound healing. Prevents and/or treats scars and skin's signs or aging promotes healing of burns, thicken skin | 1,4-Diaminobutane Dihydrochloride; Alfa Chemistry | 333-93-7 | MFR | 0.40 |
| 25 | *Pseudoalteromonas* Ferment Extract (about 12.5%), Hydrolyzed Wheat Protein (about 2.86%), Hydrolyzed Soy Protein (about 1.86%), Tripeptide-10 Citrulline (about 0.04%), Tripeptide-1 (about 0.01%), Lecithin (about 0.4%), Xanthan Gum (0.45%), Carbomer (0.028%), Triethanolamine, Phenoxyethanol (about 0.45%), Butylene Glycol (about 0.6%), Caprylyl Glycol (about 0.58%), Water (up to 100%) | Active ingredient: An anti-wrinkle active that combines peptides and proteins which increases collagen production; improves collagen organization and inhibits collagen degradation. | Trylagen ™ functional ingredient PCB; Lipotec | 820959-16-8, 94350-06-8, 68607-88-5, 960531-53-7, 72957-37-0, 8002-43-5, 11138-66-2, 9003-01-4, 102-71-6, 122-99-6, 107-88-0, 1117-86-8, N/A | MFR | 5.00 |
| 26 | Palmitoyl Tripeptide-5, Glycerin, Water | Active ingredient: Synthetic tripeptide that helps slow down the skin aging process. Simultaneously boosts collagen production and protects against collagen degradation. | Syn ™-Coll; Centerchem | 623172-56-6, 56-81-5, N/A | MFR | 2.00 |
| | | | Part E | | | |
| 27 | Palmitoyl Tripeptide-5, Panthenol, Sodium Hyaluronate, Dunaliella Salina Extract, Phenoxyethanol, Citric Acid, Sodium Benzoate, Ethylhexylglycerin, Potassium Sorbate, Pantolactone, Water | Active ingredient: Reduces the appearance of lines and wrinkles; Reduces the appearance of dark circles; Improves the skin's texture and smooths the delicate skin eye area; Moisturizes, and protects the skin.<br>Excipients:<br>Ethylhexylglycerin: week preservative, deodorant and skin conditioning agent | SYN ®-EYE; Centerchem | 623172-56-5, 81-13-0, 9067-32-7, 92128-82-0, 122-99-6, 77-92-9, 532-32-1, 70445-33-9, 24634-61-5, | MFR | 1.00 |

TABLE 2-continued

| Exemplary 0.4% putrescine and Vitamin C (0.05%) eye cream | | | | | | |
|---|---|---|---|---|---|---|
| | Ingredients (INCI Name) | Function(s) | Ingredients (Trade Name and Manufacturer) | CAS# | Grade | Amount (% W/W) |
| | | Pantolactone: Skin conditioning agent-Humectant<br>Phenoxyethanol, sodium benzoate and potassium sorbate: preservatives<br>Carbomer: Emulsion Stabilizer; Viscosity increasing agent | | 599-04-2 | | |
| 28 | Leontopodium Alpinum Callus Culture Extract, Glycerin, Xanthan Gum | Active ingredient: Reduces sagginess and improves skin | Majestem ™; Croda Canada (FR 3 031 454 - WO2016/113659) | 391900-47-3, 56-81-5, 11138-66-2 | MFR | 3.00 |
| | | | | | | 100% |

The above formulation was prepared by adding, in a suitable main stainless-steel tank equipped with a lightening type propeller mixer, all ingredients as indicated in Table 3 until the composition became clear and all ingredients have dissolved. Part A ingredients were combined in the main tank at 65-70 °C under constant mixing. Part B was prepared in a separate tank at the same temperature, under mixing. Part B was added to Part A and cooled at 5000. Part C, was next added to Part A-B and cooled to 40 °C under mixing and homogenizing. Part D (putrescine/water) was prepared in a separate tank, mixed and added to Part A-B-C. Then, remaining ingredients of part D were added under mixing, followed by Part E (one ingredient at a time). The final mixture was cooled to 3000. Platine grey bottle (15 ml AS15 S/PP) with metalized cap and airless pump were used to store the finish product to reduce product contact with ambient light. The pH of the final composition was about 7.29 (may range from 6.8 to 7.5).

TABLE 3

| Process for preparing the eye cream formulation of Table 2 | |
|---|---|
| Step | Manufacturing Process |
| 1 | Sprinkle item 2 (Magnesium Aluminum Silicate) into item 1 (water) while vortexing. Mix for about 20 minutes. |
| 2 | Mix item 3 (Xanthan Gum) with item 4 (Triethanolamine) and add to main batch with mixing. Mix for an additional about 20 minutes. |
| 3 | Add remaining ingredients in Part A and heat to about 65-70 degrees C. |
| 4 | In a secondary manufacturing tank equipped with a mixer, add the ingredients as listed under Part B and Heat to about 65-70 degrees C. Mix until obtaining a homogenous mixture. |
| 5 | Add Part B to Part A under homogenization. |
| 6 | Homogenize for about 20 minutes at high speed until smooth and uniform. |
| 7 | Cool product to about 50 degrees C. while maintaining homogenization. |
| 8 | Add Part C one item at a time while mixing and homogenizing to main batch. |
| 9 | Homogenize for about 3-5 minutes at high speed until smooth and uniform. |
| 10 | Cool batch at about 40 degrees C. with mixing and homogenizing. |
| 11 | In a separate container, dissolve item 24 (1,4-Diaminobutane Dihydrochloride) into item 23 (water) (Part D) and add to main batch. Then add remaining ingredients listed under Part D while mixing. |
| 12 | Follow with Part E. Add one item at a time, in the order listed. Keep mixing. |
| 13 | Switch to sweep mixing and cool product. |
| 14 | Cool and side sweep mix until about 30 degrees C. |

Example 2

Complex Neck Cream Comprising Multiple Active Ingredients Including Putrescine and Vitamin C

TABLE 4

| Exemplary 0.4% putrescine neck cream | | | | | | | |
|---|---|---|---|---|---|---|---|
| | Ingredients (INCI Name) | Function(s) | Ingredients (Trade Name and Manufacturer) | CAS# | Grade | Amount % W/W | Amount % W/W |
| Part A | | | | | | | |
| 1 | Water | Diluent/carrier | Purified Water | N/A | USP | 56.95 | 54.90 |
| 2 | Magnesium Aluminum Silicate | Viscosity increasing agent; Absorbent; Anticaking agent; Opacifying agent; Slip modifier | Veegum ™ Ultra; RT Vanderbilt(Cambrian) | 12199-37-0, 13463-67-7, 14808-60-7 | MFR | 1.00 | 1.00 |

TABLE 4-continued

Exemplary 0.4% putrescine neck cream

| | Ingredients (INCI Name) | Function(s) | Ingredients (Trade Name and Manufacturer) | CAS# | Grade | Amount % W/W | Amount % W/W |
|---|---|---|---|---|---|---|---|
| 3 | Xanthan Gum | Binder; Emulsion Stabilizer (gel forming); Skin conditioning agent; Surfactant - Emulsifying agent; Viscosity increasing agent | Jungbunzlauer Xanthan Gum; LV Lomas | 11138-66-2 | MFR | 0.20 | 0.20 |
| 4 | Triethanolamine | Surfactant and pH adjusting chemical (buffer); Emulsifying agent | Triethanolamine; Canada Colors and Chemicals | 102-71-6 | MFR | 0.30 | 0.30 |
| 5 | TetraSodium EDTA | Chelating agent | Versene ™ 220; Canada Colors and Chemicals | 8013-51-2 | MFR | 0.20 | 0.20 |
| | | | Part B | | | | |
| 6 | Behenyl Alcohol | Binder; emollient, emulsifier and viscosity Increasing (thickener). | Lanette ™ 22; Pachem Distribution (BASF) | 661-19-8 | MFR | 1.50 | 1.50 |
| 7 | Cetyl Palmitate (Lipid composed of cetyl alcohol and palmitic acid) | Skin conditioning agent - Emollient; Occlusive; | Trivent ™ CP; Alzo International | 540-10-3 | MFR | 1.50 | 1.50 |
| 8 | Glyceryl Stearate (40-60%), PEG-100 Stearate (40-60%) | Humectants, solvents, binders, emulsion stabilizers, and viscosity increasing agents | Lipomulse ™ 165; Tempo Canada | 123-94-4, 9004-99-3 | MFR | 4.00 | 4.00 |
| 9 | Stearic Acid (naturally occurring fatty acid) | Surfactant - emulsifying agent; refatting | Stearic Acid; Univar | 57-11-4 | MFR | 0.50 | 0.50 |
| 10 | Butylated Hydroxy Toluene | Preservative; antioxidant; | BHT; Andicor Specialty Chemicals (Evonik) | 128-37-0 | MFR | 0.10 | 0.10 |
| 11 | Butyrospermum Parkii (Shea) Butter Extract | Active ingredient: Skin conditioning | Cetiol ™ SB-45/Fancol Shea Butter; Pachem (Cognis)/ Unipex Solution (Elementis) | 68920-03-6 | MFR | 2.00 | 2.00 |
| 12 | Dimethicone | Lubricant and skin conditioning agent; occlusive; skin protectant; emollient. | DC 200/350/Element 14 PDMS 350; Canada Colors and Chemicals (Momentive) | 9006-65-9 or 63148-62-9 | MFR | 2.00 | 2.00 |
| 13 | Argania Spinosa Kernel Oil | Active ingredient: Skin conditioning agent - emollient; occlusive; | Argan Oil; Centerchem (DSM) | 223747-87-3 | MFR | 1.00 | 1.00 |
| 14 | Squalane (vegetable source; squalene hydrogenation from olive oil.) | Active ingredient: Lubricant on the skin surface. Skin conditioning agent with refatting properties - occlusive; emollient. | Keteol ™ V; Pachem Distribution | 111-01-3 | MFR | 4.00 | 4.00 |
| 15 | Caprylic/Capric Triglyceride, Titanium Dioxide, Triethoxy-caprylylsilane, Castor Oil Phosphate | Caprylic/Capric Triglyceride: Fragrance Ingredient, Skin conditioning agent-Occlusive<br>Titanium dioxide: Colorant; Opacifying agent; Sunscreen agent; Ultraviolet Light Absorber<br>Triethoxycaprylylsilane: binder<br>Castor Oil Phosphate: anticaking agent, emulsion stabilizer | 50% Ultrafine $TiO_2$ in Caprylic/Capric Triglyceride Dispersion (R3214, Sensient, discontinued and replaced by Sensient Covascreen ™); | 65381-09-1, 13463-67-7, 2943-75-1, 68308-61-2 | MFR | 1.50 | 1.50 |
| 16 | Di-C12-15 Alkyl Fumarate (U.S. Pat. No. 5,840,285) | Active ingredient Skin conditioning agent - Emollient; solvent | Marrix ™ SF; Alzo International | 142104-11-8 | MFR | 1.00 | 1.00 |
| | | | Part C | | | | |
| 17 | Cyclopentasiloxane, Dimethiconol | Skin conditioning agent - emollient; moisturizer; solvent. Improves wet and dry compatibility. Exhibits improved skin feel and water resistance. Provides smooth but not greasy after feel. Possesses non-fatty and non-sticky properties | Abil ™ OSW-5; Andicor Specialty Chemicals (Evonik) | 541-02-6, 31692-79-2 | MFR | 1.00 | 1.00 |
| 18 | Acrylates/ Acrylamide Copolymer (about 26-28%), Mineral Oil (about 22-24%), and Polysorbate 85 (1-3%), water (up to 100% i.e., 45-51%) | Emulsifier; rheology modifier<br>27% solids, liquid, pre-neutralized polymer dispersed in oil. It is a multifunctional polymer used in emulsions containing active ingredients with electrolytes and suspended inorganic pigments. Enhances skin feel, providing soft after feel | Novemer ™ EC-1; LV Lomas (Lubrizol) | N/A, 8042-47-5, 9005-70-3 | MFR | 1.30 | 1.30 |

TABLE 4-continued

Exemplary 0.4% putrescine neck cream

| | Ingredients (INCI Name) | Function(s) | Ingredients (Trade Name and Manufacturer) | CAS# | Grade | Amount % W/W | Amount % W/W |
|---|---|---|---|---|---|---|---|
| 19a | Diazolidinyl Urea (39.6%) Iodopropynyl Butylcarbamate (0.4%), Propylene Glycol (60%) | Broad-spectrum preservative system against Gram-positive and Gram-negative bacteria, yeast, and mold. | Liquid Germall ™ Plus preservative; Ashland (Tempo) | 78491-02-8, 55406-53-6, 57-55-6 | MFR | 0.5 | — |
| 19b | Phenoxyethanol (85-95%), Ethylhexylglycerin (7-13%) | | Euxyl ™ PE 9010 | 122-99-6, 70445-33-9 | MFR | — | 1.00 |
| 19c | 1,2-Hexanediol (25-50), Caprylyl Glycol (25-50%) | | Symdiol ™ 68 | 6920-22-5, 1117-86-8 | MFR | — | 0.60 |
| | | | Part D | | | | |
| 20 | Water | Diluent/carrier | Purified Water | N/A | USP | 5.00 | 5.00 |
| 21 | 1,4-Diaminobutane Dihydrochloride | Active ingredient: Skin regeneration. Promotes skin repair including wound healing. Prevents and/or treats scars and skin's signs or aging | 1,4 Diaminobutane Dihydrochloride/ Putrescine; Alfa Chemistry | 333-93-7 | USP | 0.40 | 0.40 |
| 22 | Allyl Methacrylates Crosspolymer, Polysorbate 20, Retinol (20.5% ± 2.0%), Butylated Hydroxy Toluene | Active ingredient: Multi-functional delivery system which provides sustained release and reduce the irritation of retinol. Anti-aging and skin rejuvenation. | Poly-pore 120RE; Amcol Health and Beauty Solutions | 182212-41-5, 9005-64-5, 68-26-8, 128-37-0 | MFR | 0.05 | 0.05 |
| 23 | *Pseudoalteromonas* Ferment Extract (12.5%), Hydrolyzed Wheat Protein (2.86%), Hydrolyzed Soy Protein (1.86%), Tripeptide-10 Citrulline (0.04%), Tripeptide-1 (0.01%), Lecithin, Xanthan Gum, Carbomer, Triethanolamine, Phenoxyethanol (0.71%), Butylene Glycol, Caprylyl Glycol, Water | Active ingredient: An anti-wrinkle active that combines peptides and proteins which increases collagen production; improves collagen organization and inhibits collagen degradation. | Trylagen ™ functional ingredient PCB; Lipotec | 820959-16-8, 94350-06-8, 68607-88-5, 960531-53-7, 72957-37-0, 8002-43-5, 11138-66-2, 9003-01-4, 102-71-6, 122-99-6, 107-88-0, 1117-86-8, N/A | MFR | 3.00 | 3.00 |
| 24 | Acetyl Tetrapeptide-2 (Aspartic acid, Lysine, Tyrosine and Valine residues), Caprylyl Glycol, Water | Active ingredient: Skin conditioning agent. Tetrapeptide which fights sagginess by enhancing key elements to the assembly of elastin and several collagens and overexpressing genes involved in cellular adhesion. It induces the expression of proteins Fibulin 5 and Lysyl Oxidase-Like 1, contributing to the organisation of elastic fibre and upregulates key genes to cellular cohesion through focal adhesions (talin, zyxin, integrins). Moreover, it induces the synthesis of elastin and collagen I. | Uplevity ™ peptide solution; Lipotec | 7732-18-5, 1117-86-8 | MFR | 1.50 | 1.50 |
| | | | Part E | | | | |
| 25 | Glycerin, Water, Coco-Glucoside, Caprylyl Glycol, Alcohol (Ethyl alcohol), Glaucine | Active ingredient: A glaucine in a water-soluble excipient that enhances skin firmness. | Bodyfit ™; Croda Canada (WO 2004/024695) | 56-81-5, 7732-18-5, 141464-42-8, 1117-86-8, 64-17-5, 475-81-0 | MFR | 4.00 | 4.00 |
| 26 | Leontopodium Alpinum Callus Culture Extract, Glycerin, Xanthan Gum | Active ingredient: Reduces sagginess and improves skin | Majestem ™; Croda Canada (FR 3 031 454 - WO 2016/113659) | 391900-47-3, 56-81-5, 11138-66-2 | MFR | 2.00 | 2.00 |
| 27 | Glycerin (used as a solvent, up to 100%), Acetylarginyl-tryptophyl | Active ingredient: Peptide solution which increases resilience and tightness. | Relistase ™ solution; Lipotec | 56-81-5, 1334583-93-5 | MFR | 3.00 | 3.00 |

TABLE 4-continued

Exemplary 0.4% putrescine neck cream

| | Ingredients (INCI Name) | Function(s) | Ingredients (Trade Name and Manufacturer) | CAS# | Grade | Amount % W/W | Amount % W/W |
|---|---|---|---|---|---|---|---|
| | Diphenylglycine (0.009-0.011%) | | | | | | |
| 28 | 3-O-Ethyl Ascorbic Acid (Vit C) | Active ingredient: Antioxidant, and wound healing agent. Increases collagen production and reduce the inflammation | Et-VC ™ | 86404-04-8 | MFR | 0.50 | 0.50 |
| 29 | Acrylates/ Acrylamide Copolymer (about 26-28%), Mineral Oil (about 22-24%), and Polysorbate 85 (1-3%), water (up to 100% i.e., 45-51%) see also # 18 above | Emulsifier; rheology modifier 27% solids, liquid, pre-neutralized polymer dispersed in oil. It is a multifunctional polymer used in emulsions containing active ingredients with electrolytes and suspended inorganic pigments. Enhances skin feel, providing soft after feel | Novemer ™ EC-1; LV Lomas (Lubrizol) | N/A, 8042-47-5, 9005-70-3 | MFR | — | 0.95 |
| | | | | | | 100% | |

The above formulations are prepared by adding, in a suitable main stainless-steel tank equipped with a lightening type propeller mixer, all ingredients as indicated in Table 5 until the composition becomes clear and all ingredients have dissolved. The propeller mixer was set to medium to high speed (held at room temperature, i.e., about 21 degrees Celsius). 40 mL acrylic double-wall bottles with airless pump were used to store the finish product to reduce product contact with ambient light. The pH of the final compositions was about 6.9 (i.e. 6.93).

TABLE 5

Process for preparing the neck cream formulation of Table 4

| Step | Manufacturing Process |
|---|---|
| 1 | Sprinkle item 2 into item 1 while vortexing. Mix for about 20 minutes. |
| 2 | Sprinkle item 3 into 1 and 2 with mixing. Mix for about an additional 20 minutes or until hydration and no fish eyes are present. |
| 3 | Add remaining ingredients in Part A and heat to about 65-70 degrees C. |
| 4 | In a separate container, add ingredients in the order listed under Part B and heat Part B to about 70 degrees C. |
| 5 | Add Part B to Part A under homogenization. |
| 6 | Homogenize for about 20 minutes at high speed till smooth and uniform. |
| 7 | Cool product to about 50 degrees C. |
| 8 | Add Part C one item at a time with mixing to main batch. |
| 9 | Homogenize for about 3-5 minutes at high speed until smooth and uniform. |
| 10 | Dissolve item 21 into item 20, then disperse and wet item 22 into items 20 & 21 (Part D) and add to main batch at about 40 degrees C. with mixing. |
| 11 | Then add remaining ingredients listed under Part D while mixing. |
| 12 | Add ingredients listed under Part E. Add one item at a time in the order listed with mixing. |
| 13 | Switch to sweep mixing and cool product. |
| 14 | Cool and side sweep mix until about 30 degrees C. |

Example 3

Complex Body Cream Compositions Comprising Putrescine and Vitamin C

TABLE 6

Exemplary body cream formulations

| item | Ingredients (INCI Name) | Function(s) | Ingredients (Trade Name and Manufacturer) | CAS# | Grade | Formulation (A) Amount % W/W | Formulation (B) | Formulation (C) |
|---|---|---|---|---|---|---|---|---|
| | | | Part A | | | | | |
| 1 | Water | Diluent/carrier | Purified Water USP; | N/A | USP | 62.81 | 65.40 | 63.80 |

TABLE 6-continued

| | | | | | | | | |
|---|---|---|---|---|---|---|---|---|
| Exemplary body cream formulations | | | | | | | | |
| item | Ingredients (INCI Name) | Function(s) | Ingredients (Trade Name and Manufacturer) | CAS# | Grade | Formu-lation (A) Amount % W/W | Formu-lation (B) | Formu-lation (C) |
| 2 | Magnesium Aluminum Silicate | Viscosity increasing agent; Absorbent; Anticaking agent; Opacifying agent; Slip modifier | Veegum ™ Ultra | 12199-37-0, 13463-67-7, 14808-60-7 | MFR | 1.00 | 1.00 | 1.00 |
| 3 | Xanthan Gum | Binder; Emulsion Stabilizer (gel forming); Skin conditioning agent; Surfactant-Emulsifying agent; Viscosity increasing agent | Jungbunzlauer Xanthan Gum | 11138-66-2 | MFR | 0.20 | 0.20 | 0.20 |
| 4 | Triethanolamine | Surfactant and pH adjusting chemical (buffer); Emulsifying agent | Triethanolamine | 102-71-6 | MFR | 0.30 | 0.30 | 0.30 |
| 5 | TetraSodium EDTA | Chelating agent | Versene ™ 220 | 8013-51-2 | MFR | 0.20 | 0.20 | 0.20 |
| Part B | | | | | | | | |
| 6 | Behenyl Alcohol | Binder; emollient, emulsifier and viscosity Increasing (thickener). | Lanette ™ 22 | 661-19-8 | MFR | 1.50 | 1.50 | 1.50 |
| 7 | Cetyl Palmitate | Skin conditioning agent - Emollient; Occlusive; | Trivent ™ CP | 540-10-3 | MFR | 1.50 | 1.50 | 1.50 |
| 8 | Glyceryl Stearate, PEG-100 Stearate | Humectants, solvents, binders, emulsion stabilizers, and viscosity increasing agents | Lipomulse ™ 165 | 123-94-4, 9004-99-3 | MFR | 4.00 | 4.00 | 4.00 |
| 9 | Stearic Acid | Surfactant - emulsifying agent; refatting | Stearic Acid | 57-11-4 | MFR | 0.50 | 0.50 | 0.50 |
| 10 | Butylated Hydroxytoluene | Preservative; antioxidant; | BHT | 128-37-0 | MFR | 0.10 | 0.10 | 0.10 |
| 11 | Butyrospermum Parkii (Shea) Butter Extract | Active ingredient: Skin conditioning | Cetiol ™ SB-45/ Fancol Shea Butter | 68920-03-6 | MFR | 2.00 | 2.00 | 2.00 |
| 12 | Dimethicone | Lubricant and skin conditioning agent; occlusive; skin protectant; emollient. | DC 200/350/ Element14 PDMS 350 | 9006-65-9 or 63148-62-9 | MFR | 1.00 | 1.00 | 1.00 |
| 13 | Argania Spinosa Kernel Oil | Active ingredient: Skin conditioning agent - emollient; occlusive; | Argan Oil | 223747-87-3 | MFR | 1.00 | 1.00 | 1.00 |
| 14 | Squalane | Active ingredient: Lubricant on the skin surface. Skin conditioning agent with refatting properties - occlusive; emollient. | Keteol ™ V | 111-01-3 | MFR | 4.00 | 4.00 | 4.00 |
| 15 | Caprylic/Capric Triglyceride, Titanium Dioxide, Triethoxy-caprylylsilane, Castor Oil Phosphate | Caprylic/Capric Triglyceride: Fragrance Ingredient, Skin conditioning agent - Occlusive Titanium dioxide: Colorant; Opacifying agent; Sunscreen agent; Ultraviolet Light Absorber Triethoxycaprylylsilane: binder Castor Oil Phosphate: anticaking agent, emulsion stabilizer | 50% Ultrafine TiO2 in Caprylic/Capric Triglyceride Dispersion (R3214, Sensient - Product discontinued and replaced by Sensient Covascreen ™ UVR CCT product code: 251351). | 65381-09-1, 13463-67-7, 2943-75-1, 68308-61-2 | MFR | 1.50 | 1.50 | 1.50 |
| 16 | Di-C12-15 Alkyl Fumarate (U.S. Pat. No. 5,840,285) | Active ingredient Skin conditioning agent - Emollient; solvent | Marrix ™ SF | 142104-11-8 | MFR | 1.00 | 1.00 | 1.00 |
| Part C1 | | | | | | | | |
| 17 | Water | Diluent/carrier | Purified Water USP | N/A | USP | 2.50 | — | — |
| 18 | Hexamidine Diisethionate | Antifoaming; skin conditioning; emollient; preservative | Elastab ™ HP 100/ Minox ™ HD | 659-40-5 | MFR | 0.09 | — | — |

TABLE 6-continued

| item | Ingredients (INCI Name) | Function(s) | Ingredients (Trade Name and Manufacturer) | CAS# | Grade | Formulation (A) Amount % W/W | Formulation (B) | Formulation (C) |
|---|---|---|---|---|---|---|---|---|
| | | | Exemplary body cream formulations | | | | | |
| | | | Part D1/Part C2 | | | | | |
| 19 | Cyclopentasiloxane, Dimethiconol | Skin conditioning agent - emollient; moisturizer; stabilizer and solvent. Improves wet and dry compatibility. Exhibits improved skin feel and water resistance. Provides smooth but not greasy after feel. Possesses non- fatty and non-sticky properties | Abil ™ OSW-5 | 541-02-6, 31692-79-2 | MFR | 1.00 | 1.00 | 1.00 |
| 20 | Acrylates/Acrylamide Copolymer (about 26-28%), Mineral Oil (about 22-24%), and Polysorbate 85 (1-3%), water (up to 100% i.e., 45-51%) (see also item 34 below) | Emulsifier; rheology modifier 27% solids, liquid, pre-neutralized polymer dispersed in oil. It is a multifunctional polymer used in emulsions containing active ingredients with electrolytes and suspended inorganic pigments. Enhances skin feel, providing soft after feel | Novemer ™ EC-1 | N/A, 8042-47-5, 9005-70-3 | MFR | 1.00 | 1.00 | 1.00 |
| 21 | Diazolidinyl Urea, lodopropynyl Butylcarbamate, Propylene Glycol | Broad-spectrum preservative system against Gram-positive and Gram-negative bacteria, yeast, and mold. | Liquid Germall ™ Plus preservative | 78491-02-8, 55406-53-6, 57-55-6 | MFR | 0.50 | 0.50 | — |
| | | | Part C3 (formulation (C) only) | | | | | |
| 22 | Phenoxyethanol (85-95%), Ethylhexylglycerin (7-13%) | Preservative | Eukyl ™ PE 9010 | 122-99-6, 70445-33-9 | MFR | — | — | 1.00 |
| 23 | 1,2-Hexanediol (25-50), Caprylyl Glycol (25-50%) | Preservative | Symdiol ™ 68 | 6920-22-5, 1117-86-8 | MFR | — | — | 0.60 |
| | | | Part E/Part D2 | | | | | |
| 24 | Water | Diluent/Carrier | Purified Water USP | N/A | USP | 2.50 | 2.50 | 2.50 |
| 25 | Allyl Methacrylates Crosspolymer, Polysorbate 20, Retinol, Butylated Hydroxytoluene | Active ingredient: Multi-functional delivery system which provides sustained release and reduce the irritation of retinol. Anti-aging and skin rejuvenation. | Poly-pore 120RE | 182212-41-5, 9005-64-5, 68-26-8, 128-37-0 | MFR | 0.05 | 0.05 | 0.05 |
| 26 | *Pseudoalteromonas* Ferment Extract (12.5%), Hydrolyzed Wheat Protein (2.86%), Hydrolyzed Soy Protein (1.86%), Tripeptide-10 Citrulline (0.04%), Tripeptide-1 (0.01%), Lecithin, Xanthan Gum, Carbomer, Triethanolamine, Phenoxyethanol (0.71%), Butylene Glycol, Caprylyl Glycol, Water | Active ingredient: An anti-wrinkle active that combines peptides and proteins which increases collagen production; improves collagen organization and inhibits collagen degradation. | Trylagen ™ functional ingredient PCB | 820959-16-8, 94350-06-8, 68607-88-5, 960531-53-7, 72957-37-0, 8002-43-5, 11138-66-2, 9003-01-4, 102-71-6, 122-99-6, 107-88-0, 1117-86-8, N/A | MFR | 1.50 | 1.50 | 1.50 |
| 27 | Water (up to 100%), Soluble Collagen (0.8-1%), Sodium Hyaluronate (0.09-011%) | Active ingredient Skin conditioning agent, humectant, skin hydration. In the presence of water Hyaluronic acid resume a spherical coiled shape binding and immobilizing water and conferring a superior smoothness to the skin. Native soluble collagen molecules are long linear | Collagen-Hyal ™ | N/A, 9067-32-7 | MFR | 2.50 | 2.50 | 2.50 |

TABLE 6-continued

| item | Ingredients (INCI Name) | Function(s) | Ingredients (Trade Name and Manufacturer) | CAS# | Grade | Formulation (A) Amount % W/W | Formulation (B) | Formulation (C) |
|---|---|---|---|---|---|---|---|---|
| Exemplary body cream formulations | | | | | | | | |
| | | coils and form a thin hydrated film on the skin surface. The complexation of these two actives by means of a special proceeding provides a powerful hydration factor. | | | | | | |
| 28 | Hydroxyresveratrol (1.0-3.0%), Polyglyceryl-10 Oleate (20.0-25.0%), Polyglyceryl-6 Laurate (12.0-16.0%), Sorbitan Palmitate (6.0-8.0%), Dicetyl Phosphate (6.0-8.0%), Water (45.0-50.0%) | Active ingredient: inhibitor of tyrosinase (enzyme which catalyzes the rate limiting step in melanin synthesis. Skin lightener. | NIO-Oxy | 4721-07-7, 79665-93-3, 51033-38-6, 26266-57-9, 2197-63-9, N/A | MFR | 1.00 | 1.00 | 1.00 |
| 29 | Water, Hydrolyzed Milk Protein (casein and free amino acids, average molecular weight of 2500 Daltons and about 20% of free amino acids) | Active ingredient. Skin conditioning and film-forming properties, and moisturising and protecting effects. | Kelimilk ™ (Liquid) | 92797-39-2 | MFR | 2.00 | 2.00 | 2.00 |
| 30 | Leontopodium Alpinum Callus Culture Extract, Glycerin, Xanthan Gum | Active ingredient: Reduces sagginess and improves skin | Majestem ™ (FR 3 031 454 - WO 2016/113659) | 391900-47-3, 56-81-5, 11138-66-2 | MFR | 1.00 | 1.00 | 1.00 |
| 31 | 3-O-Ethyl Ascorbic Acid | Active ingredient: Antioxidant, and wound healing agent. Increases collagen production and reduce the inflammation | Et-VC ™ | 86404-04-8 | MFR | 0.50 | 0.50 | 0.50 |
| 32 | 1,4-Diaminobutane Dihydrochloride | Active ingredient: Skin regeneration. Promotes skin repair including wound healing. Prevents and/or treats scars and skin's signs or aging | 1,4-Diaminobutane Dihydrochloride; Alfa Chemistry | 333-93-7 | USP | 0.40 | 0.40 | 0.40 |
| 33 | Hydrolyzed Sodium Hyaluronate (<10 kDa) | Active ingredient. Moisturizing, repairing cells damaged by UV, scavenging free radical and anti-aging. | MiniHA ™ (HA-Oligo degraded by hyaluronidase) | 9067-32-7 | MFR | 0.30 | 0.30 | 0.30 |
| 34 | Mica, Titanium Dioxide | pearlescent and iridescent pigment | Flamenco Satina 120T | 12001-26-2, 134-67-7 | MFR | 0.50 | 0.50 | 0.50 |
| 35 | Fragrance | N.A. | Petal Blush Sozio SZ1821OP | N/A | MFR | 0.05 | 0.05 | 0.05 |
| Part E2 | | | | | | | | |
| 36 | Acrylates/Acrylamide Copolymer (about 26-28%), Mineral Oil (about 22-24%), and Polysorbate 85 (1-3%), water (up to 100% i.e., 45-51%) | See item # 20 above | Novemer ™ EC-1 | | MFR | — | — | 0.5 |
| pH: | | | | | | 6.62 | 6.62 | 6.62 |
| | | | | | | 100 | 100 | 100 |

The above formulations were prepared by adding, in a suitable stainless-steel tank equipped with a lightening type propeller mixer, all ingredients as indicated in Table 6 until the composition became clear and all ingredients have dissolved. The propeller mixer was set to medium to high speed (held at room temperature, i.e., about 21 degrees Celsius). AS200J/PP 200 mL Moldey grey PMS 80, metallic coating PMS877C, protective coating, silkscreen PMS426, hot stamp shiny silver airless pump bottle containers were used to store the finish product to reduce product contact with ambient light. A nitrogen blanket and yellow light was used for Part E until the end of the manufacturing process. The pH of the final compositions was between about 6.5 to 7.5.

The main differences between formulations (A), (B) and (C) described in Table 6 reside in the type of preservative system used. In Formula (A) of Table 6 a combination of hexamidine diisethionate (Part C, item 18) and broad spectrum preservative system (Diazolidinyl Urea, Iodopropynyl Butylcarbamate, Propylene Glycol (Germall Plus, Item 21 in Table 6)) is used. Formula (B) is identical to Formula (A), except that hexamidine diisethionate (Part C, item 18) is not present (removed because discontinued). Formula (C) uses a further alternative preservative system comprising a first preservative agent comprised of Phenoxyethanol (85-95% and Ethylhexylglycerin (7-13%) and a second preservative agent comprising 1,2-hexanediol and caprylyl glycol. All formulations ((A), (B) and (C)) comprise butylated hydroxytoluene as a further preservative agent which is also an antioxidant.

TABLE 7

Process for preparing the body cream Formulation (A) of Table 6

| Step# | Manufacturing Process |
|---|---|
| N.B. | Manufactured using a Nitrogen blanket and yellow light from Step 11 (Part E/D2 until the end) |
| 1 | Sprinkle item 2 into item 1 while vortexing. Mix for about 20 minutes. |
| 2 | Sprinkle item 3 into 1 and 2 while mixing. Mix for about an additional 20 minutes or until hydration and no fish eyes are present. |
| 3 | Add remaining ingredients in Part A and heat to about 65-70 degrees C. |
| 4 | In a separate container, add ingredients in the order listed under Part B and heat Part B to about 70 degrees C. |
| 5 | Add Part B to Part A with homogenization. |
| 6 | Homogenize for about 20 minutes at high speed till smooth and uniform. |
| 7 | Cool product to about 50 degrees C. |
| 8 | Heat ingredients listed under part C1 together to about 75-80 degrees C. and until all dissolved and clear and compensate for water loss, if necessary. Set aside to use later in the procedure. |
| 9 | Add Part D1 one item at a time with mixing to main batch (Parts A and B). |
| 10 | Homogenize for 3-5 minutes at high speed until smooth and uniform. |
| 11 | Prepare Part E |
| 12 | Wet and dissolve item 23 into item 22 (Part E), then add the remaining ingredients one by one to Part E while mixing in between additions until homogenous. Then, add to main batch at 40 degrees C. with mixing. |
| 13 | Now add Part C1 to Part A/B/D1/E with mixing. |
| 13 | Switch to sweep mixing and cool product. |
| 14 | Cool and side sweep mix until about 30 degrees C. |

TABLE 8

Process for preparing the body cream Formulation (B) of Table 6:

| Step# | Manufacturing Process |
|---|---|
| N.B. | Manufacture using a Nitrogen blanket and yellow light from Step 11 (Part E until the end) |
| 1 | Sprinkle item 2 into item 1 while vortexing. Mix for about 20 minutes. |
| 2 | Sprinkle item 3 into 1 and 2 with mixing. Mix for about an additional 20 minutes or until hydration and no fish eyes are present. |
| 3 | Add remaining ingredients in Part A and heat to about 65-70 degrees C. |
| 4 | In a separate container, add ingredients in the order listed under Part B and heat Part B to about 70 degrees C. |
| 5 | Add Part B to Part A with homogenization. |
| 6 | Homogenize for about 20 minutes at high speed till smooth and uniform. |
| 7 | Cool product to about 50 degrees C. |
| 8 | Heat ingredients listed under part C together to 75-80 degrees C. and until all dissolved and clear and compensate for water loss, if necessary. Set aside to use later in the procedure. |
| 9 | Add Part C2 one item at a time with mixing to main batch (Parts A and B). |
| 10 | Homogenize for about 3-5 minutes at high speed until smooth and uniform. |
| 11 | Prepare Part E/Part D2 |
| 12 | Wet and dissolve item 21 into item 20 (Part D2) then add to main batch at about 40 degrees C. with mixing. Then add the remaining ingredients one by one listed under Part D2 while mixing in between additions until homogenous. |
| 13 | Now add Part C to Part A/B/D/E with mixing. |
| 14 | Switch to sweep mixing and cool product. |
| 15 | Cool and side sweep mix until about 30 degrees C. |

TABLE 9

Process for preparing body cream Formulation (C) of Table 6:

| Step# | Manufacturing Procedure |
|---|---|
| N.B. | Manufacture using a Nitrogen blanket and yellow light from Step 11 (Part E until the end) |
| 1 | Sprinkle item 2 into item 1 while vortexing. Mix for about 20 minutes. |
| 2 | Sprinkle item 3 into 1 and 2 while mixing. Mix for about an additional 20 minutes or until hydration and no fish eyes are present. |
| 3 | Add remaining ingredients in Part A and heat to about 65-70 degrees C. |
| 4 | In a separate container, add ingredients in the order listed under Part B and heat Part B to about 70 degrees C. |
| 5 | Add Part B to Part A with homogenization. |
| 6 | Homogenize for about 20 minutes at high speed till smooth and uniform. |
| 7 | Cool product to about 50 degrees C. |
| 8 | Add ingredients listed under Part C2: one by one mixing in between addition followed by about 10-15 minutes of homogenization and circulation. Formulation will thicken. |
| 9 | Add Part C3 one item at a time while mixing to main batch (Part A/B/C2). |
| 10 | Homogenize for about 3-5 minutes at high speed until smooth and uniform. Then cool main batch to about 40 degrees C. |
| 11 | Prepare Part D2 (during cooling). |

TABLE 9-continued

| Process for preparing body cream Formulation (C) of Table 6: | |
|---|---|
| Step# | Manufacturing Procedure |
| 12 | Wet and dissolve item 22 into item 21 (Part D2), then add the remaining ingredients one by one to Part D2 while mixing in between additions until homogenous. Then add to main batch at about 40 degrees C. with mixing. |
| 13 | Now add Part E2 to Part A/B/C2/C3/D2 with mixing. Then homogenize about 10-15 with circulation to achieve desired. |
| 14 | Switch to sweep mixing and cool product. |
| 15 | Cool and side sweep mix until about 30 degrees C. |

Example 4

Stability of Compositions of the Present Invention

Preliminary stability tests of compositions of the present invention comprising putrescine (0.4%/) together with Retinol, and optionally Vitamin C (e.g. 0.05%, 0.5%, 1%, or more of 3-O-3thyl Ascorbic acid and/or ascorbyl palmitate) show that the compositions are stable. Indeed, no significant change in color, odor, pH and texture (including absence of multiple phases, and precipitate) were observed. Further stability tests were conducted at 25 °C in an atmosphere of +/−2% to 75% relative humidity as detailed in Table 10 below.

TABLE 10

Stability program designed for putrescine and Vitamin C formulations 25° C. +/−2 to 75% relative humidity

| Observed characteristic | Time Points (in months): 0 | 3 | 6 | 9 | 12 | 18 | 24 | 30 | 36 | 42 | 48 |
|---|---|---|---|---|---|---|---|---|---|---|---|
| Organoleptic | C | C | C | C | C | C | C | C | C | C | C |
| pH: USP <791>: [1] | C | C | C | C | C | C | C | C | C | C | C |
| Viscosity: USP <912>: [2] | C | C | C | C | C | C | C | C | C | C | C |
| Putrescine level: HPLC Method[3] | C | C | C | C | C | C | C | C | C | C | C |
| Microbiology; USP<61>[4] and USP<62>[5] | C | C | C | C | C | C | C | C | C | C | C |

C = Results conform to specifications.

[1] The pH value similar to the initial one overtime ±10%.

[2] The Viscosity similar to the initial one over time ±10%.

[3] The Putrescine ±10% of the initial concentration of the formula

[4] USP<61> = Total Aerobic Count <100 cfu/g and yeasts and moulds <100 cfu/g

[5] USP<62> = *S. aureus*, *P. aeruginosa*, *E. coli*, *Salmonella* sp all absent.

The scope of the claims should not be limited by the preferred embodiments set forth in the examples, but should be given the broadest interpretation consistent with the description as a whole.

REFERENCES

1. Tajima S, Pinnell S R, Ascorbic acid preferentially enhances type I and III collagen transcription in human skin fibroblasts. J. Derm Science. 11:250-53, 1996. 2Traikovich S S.
2. Use of topical ascorbic acid and its effects on photo damaged skin topography. Arch Otolaryngol Head Neck Surg 125:1091-98, 1999.
3. Murray J, Darr D, Reich J. Pinnell S. Topical vitamin C treatment reduces ultraviolet B radiation-included erythema in human skin. J. Invest Dermatol 1991:96:587 (abstract).
4. C. W. Lynde. Moisturizers: What they are and how they work. Skin Therapy Letter, 2001; http://www.skintherapyletter.com/2001/6.13/2.html.
5. Zhang M. et al., Spermine inhibits proinflammatory cytokine synthesis in human mononuclear cells: a counterregulatory mechanism that restrains the immune response. J. Exp. Med. 185, 1759-68 (1997).
6. Soda K. et al., Spermine, a natural polyamine, suppresses LFA-1 expression on human lymphocyte. J. Immunol. 175, 237-45 (2005).
7. Soda K. et al., Polyamines' anti-aging effects. Food style 21, 10(10), 43-54 (2006).
8. Sheokand, Sunita, Anita Kumari, and Veena Sawhney. "Effect of Nitric Oxide and Putrescine on Antioxidative Responses under NaCl Stress in Chickpea Plants." Physiology and molecular biology of plants: an international journal of functional plant biology 14.4 (2008): 355-362. PMC. Web. 14 Jun. 2017.
9. Dolynchuk K N et al., Effect of Putrescine on tissue transglutaminase activity in wounds: Decreased breaking strength and increased matrix Fucoprotein solubility, Plast Reconstr. Surg. 1994; 93: page 567-573.

The invention claimed is:

1. A method of using an aqueous topical composition, by applying the aqueous topical composition having a pH between about 6.5 and about 7.5, and comprising:

(i) putrescine;

(ii) (ii-a) at least one Vitamin C or Vitamin C derivative, and/or (ii-b) at least one peptide, wherein the at least one peptide comprises (ii-bi) tripeptide 1;

(ii-bii) tripeptide 5;

(ii-biii) tripeptide 10 citrulline;

(ii-biv) tetrapeptide 2, (ii-bv) acetylarginyltryptophyl diphenylglycine or (ii-bvi) any combination of at least two of (ii-i) to (ii-bv); and (iii) (iiia) at least one viscosity increasing agent/anticaking agent, wherein the at least one viscosity increasing agent/anticaking agent comprises magnesium aluminum silicate;

(iiib) at least one a binder/stabilizer, wherein the at least one binder/stabilizer comprises xanthan gum; (iiic) at least one skin conditioning agent, wherein the at least one skin conditioning agent comprises squalane;

(iiid) at least one humectant, emulsion stabilizer, surfactant and viscosity increasing agent, wherein the at least one humectant, emulsion stabilizer, surfactant and viscosity increasing agent comprises a blend of glyceryl stearate and PEG-100 stearate;

(iiie) at least one rheology modifier, wherein the at least one rheology modifier comprises a blend of acrylates/acrylamide copolymer, mineral oil and polysorbate-85; and (iiif) at least one stabilizer which improves wet and dry compatibility and water resistance, wherein the at least one stabilizer comprises a blend of cyclopentasiloxane and dimethiconol, for (a) treating or preventing skin inflammation, skin irritation, and/or skin's signs of aging; (b) increasing skin thickness; (c) promoting wound healing; or (d) preventing or reducing the formation of hypertrophic scar tissue.

2. The method of claim 1, wherein:

said Vitamin C or Vitamin C derivative consists of L-ascorbic acid, 3-O-ethyl ascorbic acid (ETVC), ascorbyl palmitate or any combination of at least two thereof; and/or the concentration of said Vitamin C or Vitamin C derivative is between about 0.05% w/w and about 20% w/w; and/or the concentration of said at least one viscosity increasing agent/anticaking agent is between about 0.6% w/w and about 3% w/w; and/or the concentration of said at least one binder/stabilizer is between about 0.1% w/w and about 0.9% w/w; and/or the concentration of said at least one skin conditioning agent is between about 2% w/w and about 36% w/w; and/or the concentration of said at least one humectant, emulsion stabilizer, surfactant and viscosity increasing agent is between about 1% w/w and about 5% w/w; and/or the concentration of said at least one rheology modifier is between about 1% w/w and about 3% w/w; and/or the concentration of said at least one stabilizer which improves wet and dry compatibility and water resistance is between about 1% w/w and about 5% w/w; and/or the concentration of said putrescine is between about 0.1% w/w and about 2% w/w.

3. The method of claim 2, wherein the concentration of the putrescine is between about 0.4% w/w and about 0.8% w/w.

4. The method of claim 2, wherein the at least one at least one humectant, emulsion stabilizer, surfactant and viscosity increasing agent comprises the blend of glyceryl stearate and PEG-100 stearate in a ratio of between about 4:6 and about 6:4 of glyceryl stearate: PEG-100 stearate.

5. The method of claim 1, further comprising a fruit extract, a retinoid, resveratrol, tocopherol, tocopheryl acetate, retinol, retinyl palmitate, hydroquinone, proanthocyanidin, butylated hydroxytoluene, butylated hydroxyanisole, astaxanthin, alpha lipoic acid, tocotrienol, coenzyme Q10, α-hydroxy acid, kojic acid, kinetin, wine extract, vitamin K, a plant extract, resorcinol, lactic acid, salicylic acid or any combination of at least two thereof.

6. The method of claim 1, wherein the aqueous topical composition comprises between about 55% and 65% w/w of water.

* * * * *